United States Patent
Ishikawa et al.

(10) Patent No.: US 6,464,687 B1
(45) Date of Patent: Oct. 15, 2002

(54) IMPLANTABLE DRUG DELIVERY SYSTEM

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hayes, Dallas, TX (US); F. Andrew Gaffney, Nashville, TN (US)

(73) Assignee: Ball Semiconductor, Inc., Allen, TX (US)

(*) Notice: Subject to any disclaimer, the term of this patent is extended or adjusted under 35 U.S.C. 154(b) by 0 days.

(21) Appl. No.: 09/521,922

(22) Filed: Mar. 9, 2000

Related U.S. Application Data

(60) Provisional application No. 60/163,656, filed on Nov. 3, 1999, provisional application No. 60/149,799, filed on Aug. 19, 1999, provisional application No. 60/137,100, filed on Jun. 2, 1999, provisional application No. 60/137,071, filed on Jun. 2, 1999, and provisional application No. 60/123,676, filed on Mar. 9, 1999.

(51) Int. Cl.$^7$ ................................................ A61K 9/22
(52) U.S. Cl. ............................................... 604/891.1
(58) Field of Search .......................... 604/891.1, 890.1, 604/65, 67; 424/422, 83; 128/213, 260, 635; 205/665; 257/618

(56) References Cited

U.S. PATENT DOCUMENTS

| | | | | |
|---|---|---|---|---|
| 4,793,825 A | * | 12/1988 | Benjamin et al. | 600/302 |
| 5,469,846 A | * | 11/1995 | Khan | 204/403.07 |
| 5,874,214 A | * | 2/1999 | Nova et al. | 365/151 |
| 6,263,237 B1 | * | 7/2001 | Rise | 128/898 |
| 6,272,370 B1 | * | 8/2001 | Gillies et al. | 324/309 |

* cited by examiner

*Primary Examiner*—Teresa Walberg
*Assistant Examiner*—Daniel Robinson
(74) *Attorney, Agent, or Firm*—Howison, Thoma & Arnott, L.L.P.

(57) ABSTRACT

A miniature implantable drug delivery capsule system. The drug delivery system (400) comprises one or more ball semiconductor aggregations (404) and (406) facilitating release of a drug stored in a reservoir (402). The first aggregate (404) is used for sensing and memory, and a second aggregation (406) for control aspects, such as for pumping and dispensing of the drug. Notably, the aggregates (404) and (406) may be interconnected by a common bus (410) for communication purposes, or may be implemented to operate independently of each other. Each aggregate (404) and (406) is encased in a semipermeable membrane (408) to allow species which are to be monitored, and drugs to be delivered, to freely diffuse. The system (400) may communicate with a remote control system, or operate independently on local power over a long period for delivery of the drug based upon a request of the patient, timed-release under control by the system (400), or delivery in accordance with measured markers.

16 Claims, 16 Drawing Sheets

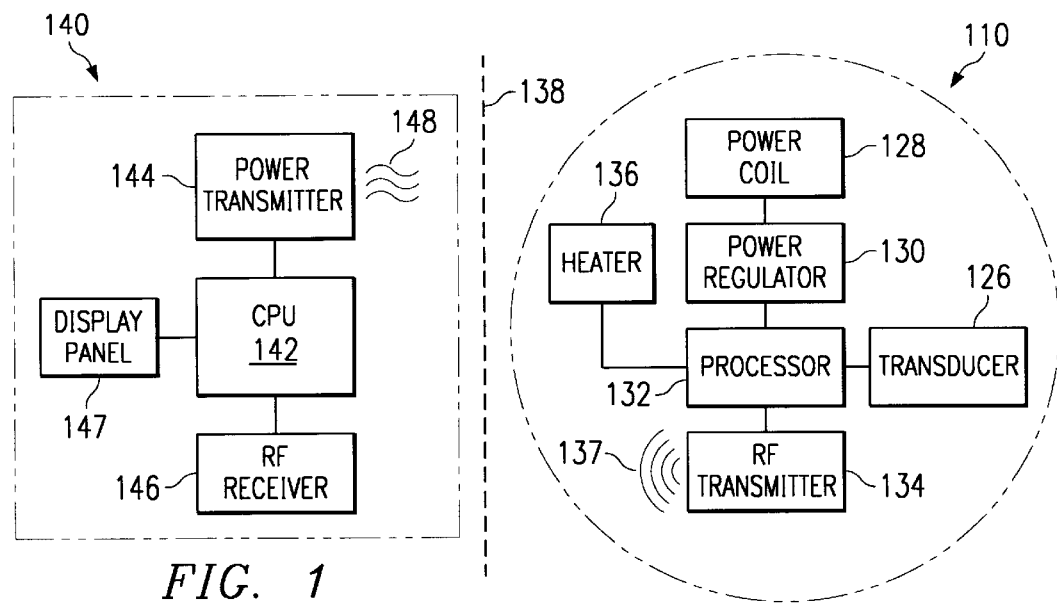
FIG. 1
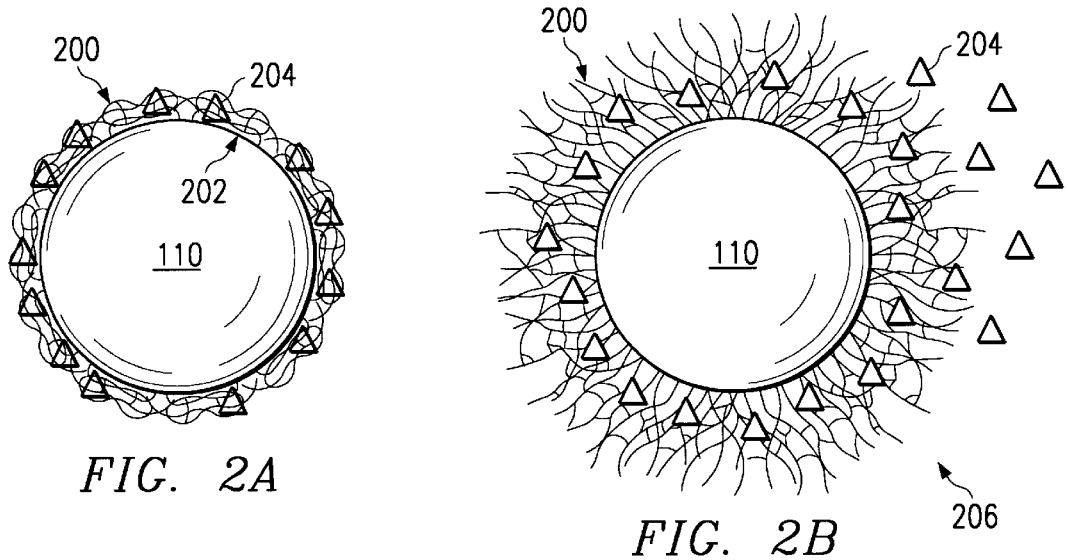
FIG. 2A
FIG. 2B
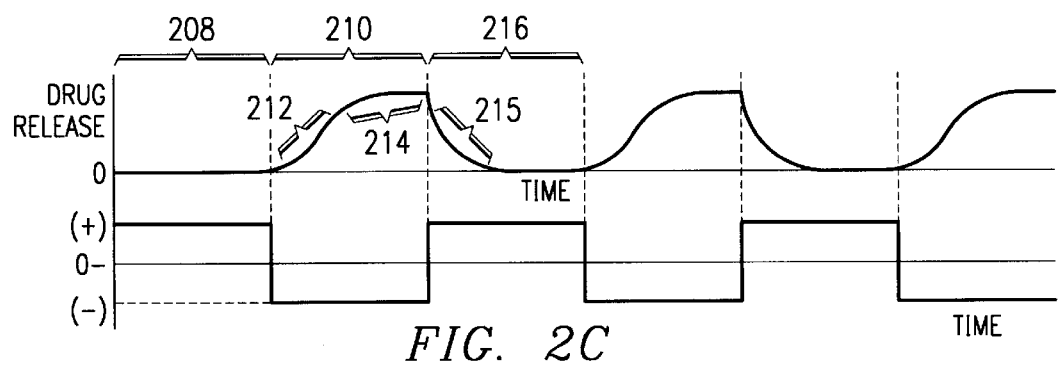
FIG. 2C

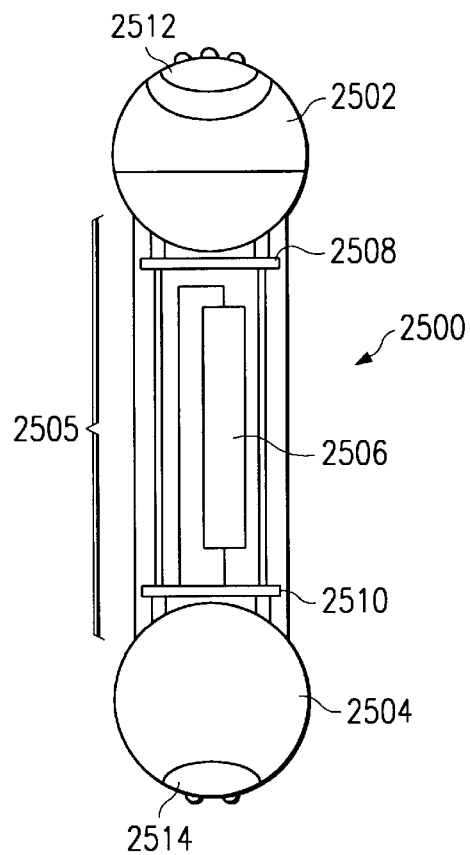
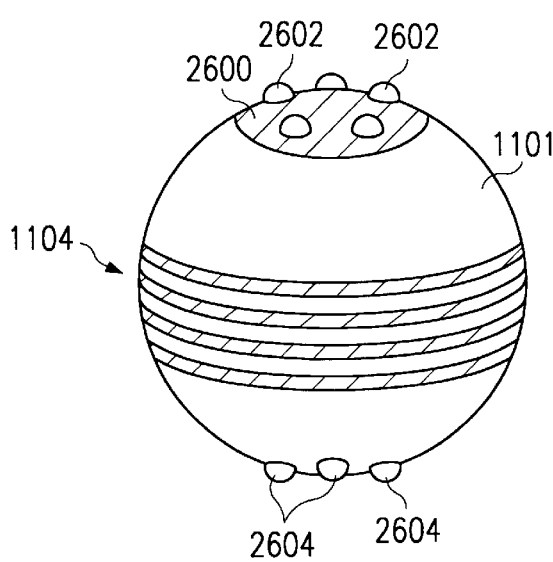
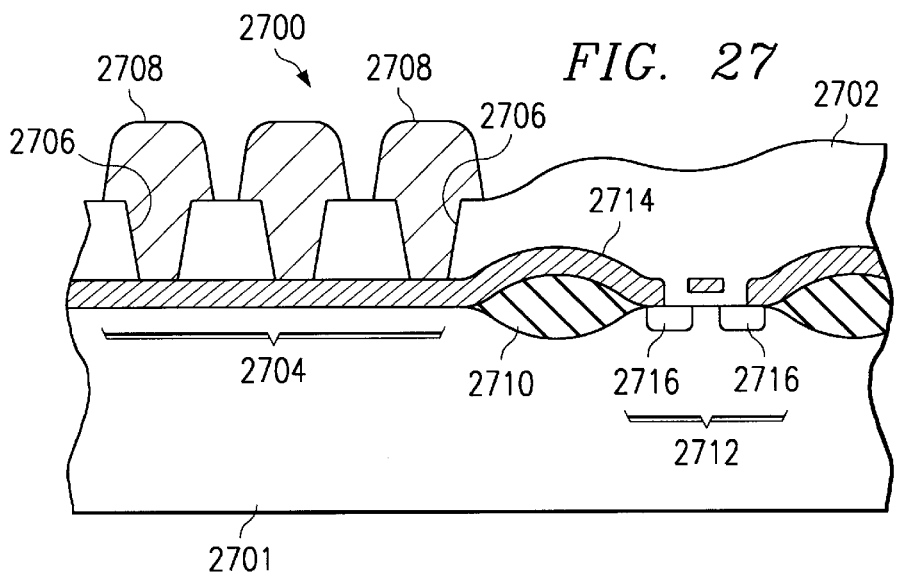

IMPLANTABLE DRUG DELIVERY SYSTEM

CROSS-REFERENCE TO RELATED APPLICATIONS

This application claims priority under 35 U.S.C §119(e) of U.S. Provisional Patent Application Ser. No. 60/123,676, entitled "IMPLANTABLE DRUG DELIVERY SYSTEM," filed Mar. 9, 1999, and is also related to U.S. Pat. No. 5,955,776 entitled "SPHERICAL-SHAPED SEMICONDUCTOR INTEGRATED CIRCUIT," issued Sep. 21, 1999, and the following pending applications: U.S. patent application Ser. No. 09/323,585 entitled "IMPLANTABLE EPICARDIAL ELECTRODE," filed Jun. 2, 1999; U.S. Provisional Patent Application Ser. No. 60/137,071 entitled "GLUCOSE SENSOR," filed Jun. 2, 1999; U.S. Provisional Patent Application Ser. No. 60/137,100 entitled "METHOD AND APPARATUS FOR ATTACHING TAGS TO MEDICAL DEVICES," filed Jun. 2, 1999; U.S. Provisional Patent Application Ser. No. 60/149,799 entitled "MINIATURE PUMP-THROUGH SENSOR MODULES," filed Aug. 19, 1999; U.S. patent application Ser. No. 09/448,641 entitled "INTRALUMINAL MONITORING SYSTEM," filed Nov. 24, 1999; U.S. patent application Ser. No. 09/448,781 entitled "SPHERICALLY-SHAPED BIOMEDICAL IC," filed Nov. 24, 1999; U.S. patent application Ser. No. 09/448,642 entitled "MINIATURE SPHERICAL-SHAPED SEMICONDUCTOR WITH TRANSDUCER," filed Nov. 24, 1999; U.S. patent application Ser. No. 09/478,320 entitled "WIRELESS EKG," filed Jan. 6, 2000; U.S. patent application Ser. No. 09/448,638 entitled "INTERNAL THERMOMETER," filed Nov. 24, 1999; U.S. patent application Ser. No. 09/448,678 entitled "METHOD OF AND SYSTEM FOR IDENTIFYING MEDICAL PRODUCTS," filed Nov. 24, 1999; U.S. patent application Ser. No. 09/448,644 entitled "MONITOR FOR INTERVENTIONAL PRODUCTS," filed Nov. 24, 1999; U.S. patent application Ser. No. 09/475,312 entitled "POSITION SENSING SYSTEM," filed Dec. 30, 1999; U.S. patent application Ser. No. 09/475,819 entitled "INJECTABLE THERMAL BALLS FOR TUMOR ABLATION," filed Dec. 30, 1999; U.S. patent application Ser. No. 09/478,592 entitled "IMPLANTABLE NEURO-STIMULATOR," filed Jan. 6, 2000; U.S. patent application Ser. No. 09/478,591 entitled "RADIATION DOSIMETRY SYSTEM," filed Jan. 6, 2000; and U.S. Provisional Patent Application Ser. No. 60/163,656 entitled "MEDICALLY IMPLANTED ACCELEROMETER," filed Nov. 3, 1999, each of which is herein incorporated by reference.

TECHNICAL FIELD OF THE INVENTION

This invention is related to body implantable systems, and more particularly to miniature electronic components for use in delivering drugs into patients.

BACKGROUND OF THE INVENTION

There is a large population of people and animals who would greatly benefit from the ability to have an implanted drug delivery device. Many delivery devices have been developed, but few have found widespread clinical use because of the large size required. Drug delivery systems have long been used to provide patients with appropriate dosages of drugs over extended periods. Implantable devices have the advantage of assuring patient compliance and delivery accuracy, as well as the ability to create high local concentrations of medications without systemic side effects such as those occurring with chemotherapeutic drugs. These advantages make local, implantable drug delivery the most effective treatment for many therapeutic regimens. This application discloses a drug delivery system based on programmable intervals similar to the following patents: U.S. Pat. No. 4,731,051 entitled "Programmable Control Means For Providing Safe And Controlled Medication Infusion," issued Mar. 15, 1988; U.S. Pat. No. 5,041,107 entitled "Electrically Controllable Non-Occluding, Body Implantable Drug Delivery System," issued Aug. 20, 1991; and U.S. Pat. No. 4,003,379 entitled "Apparatus And Method For Implanting Self-Powered Medication Dispensing," issued Jan. 18, 1977, all of the disclosures of which are herein incorporated by reference.

This application also discloses methods to deliver drugs based on a sensed physiological need, examples being described in the following patents: U.S. Pat. No. 5,474,552 entitled "Implantable Drug Delivery Pump," issued Dec. 12, 1995; U.S. Pat. No. 4,055,175 entitled "Blood Glucose Control Apparatus," issued Oct. 25, 1977; U.S. Pat. No. 5,190,041 entitled "System For Monitoring And Controlling Blood Glucose," issued Mar. 2, 1993; and U.S. Pat. No. 5,658,250 entitled "Systems And Methods For Operating Ambulatory Medical Devices Such As Drug Delivery Devices," issued Aug. 19, 1997, the contents of which are hereby incorporated by reference.

SUMMARY OF THE INVENTION

The present invention disclosed and claimed herein, in one aspect thereof, is a system for delivering a drug to a patient. The system comprises a drug storage medium for storing a drug; and one or more aggregations of semiconductor devices operatively connected to the drug storage medium for monitor and control of the dispensing of the drug. The system is then implanted in the body of the patient at a drug delivery site for delivery of the drug to said site.

BRIEF DESCRIPTION OF THE DRAWINGS

For a more complete understanding of the present invention and the advantages thereof, reference is now made to the following description taken in conjunction with the accompanying Drawings in which:

FIG. 1 illustrates a general block diagram of circuitry of a ball and remote control system;

FIG. 2A illustrates the inhibit operation of a single hydrogel ball which is coated with a hydrogel made of polyelectrolytes covalently attached to the surface of the ball;

FIG. 2B illustrates a release operation of the ball which allows the gel to bloom into the aqueous phase facilitating the diffusion of the drug into the surrounding media;

FIG. 2C illustrates a graph of the temporal changes in surface charge and expected corresponding changes in drug release;

FIG. 25 illustrates a side view of an alternate embodiment having additional circuitry where the ball provides a stimulus function for the electrical stimulation of tissues at or near the time of drug delivery;

FIG. 26 illustrates a perspective view of a thermal-sensor ball having a single transducer interface, and an inductive element illustrated as strips of conductive material wrapped around the exterior of the ball;

FIG. 27 illustrates a cross-sectional view of an output pad of the stimulus embodiment;

DETAILED DESCRIPTION OF THE INVENTION

Figure 3:
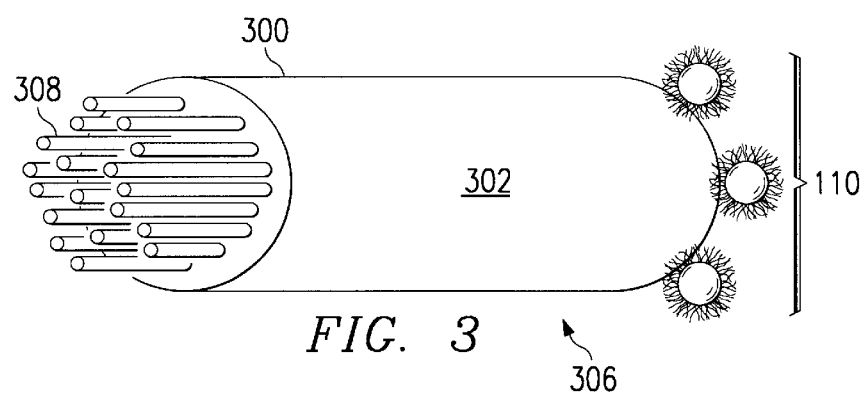
FIG. 3 illustrates a wound-healing application having a conduit for nerve regeneration with hydrogel-loaded ball semiconductors attached to the distal end.

The disclosed drug delivery embodiments comprise a multi-mode, multi-format system for metered delivery of drugs, including small molecular weight drugs, proteins, glycoproteins, plasmids, oligonucleotides, viruses, and other molecules of biological significance. Each mode of drug delivery preferably has as one component, a miniature, and substantially spherical semiconductor, or aggregate of such miniature and substantially spherical semiconductors, hereafter referred to in the singular as a "ball semiconductor" or simply as a "ball." The ball semiconductor can be programmed with internal timing and delivery logic, as well as the capability to sense a variety of physical and chemical signals.

These small ball semiconductors (e.g., approximately one millimeter in diameter) are capable of receiving power from outside sources through radio frequency transmission, and transmitting data and information outside the body also by radio frequency communication. The preferred spherical shape of these ball semiconductors provides several inherent advantages over conventional flat silicon wafers. Being approximately one millimeter, these balls are smaller than traditional semiconductor devices in common use today. The spherical shape also enhances the radio frequency (RF) capabilities compared to that of flat chip devices. The small size and continuously smooth, featureless surface also allows these ball semiconductors to be implanted with less disruption to normal tissue, and also allows them to be implanted within much more sensitive tissues such as the brain, spinal cord and the eye. This geometrical enhancement of biocompatibility allows the balls to have expanded capabilities compared with traditional flat wafer-based semiconductors. In one embodiment, the ball semiconductors receive power via RF transmission from a source located outside the body, and have the ability to be reprogrammed telemetrically for altering the timing sequence and amount of drug released at any time. In another embodiment, the balls receive power from a control system implanted in the body either proximate to or remote from the drug delivery system. The semiconductor balls can also transmit data telemetrically outside of the body, and can be interrogated non-invasively to determine the sequence history and amount of drug delivered.

Ball semiconductors can be configured to act as sensors for a number of physical signals including force, velocity, acceleration, displacement, orientation, hydrostatic pressure, osmotic pressure, fluid velocity, light, sound, and radiation; chemical signals such as glucose, $Na^+$, $K^-$, $Cl^-$, urea, bilirubin; gaseous signal such as $O_2$, $CO_2$, CO, nitrogeneous materials; as well as the ability to detect specific biological markers including proteins, drugs, DNA, RNA, glycoproteins and other biological molecules for which a receptor ligand can be made. The balls can also be made to produce light, sound, heat, and electrical charge on their surface. These ball semiconductors can also be programmed as microprocessors and have the ability to store data in memory. They are readily reprogrammed by telemetry, following implantation. Some capabilities of the ball semiconductor have already been sufficiently described in the above cross-related and commonly assigned patent applications.

Some of the capabilities of these ball semiconductors are described in the following U.S. Pat. No. 5,955,776 entitled "Spherical-Shaped Semiconductor Integrated Circuit," issued Sep. 21, 1999, and pending U.S. patent applications Ser. No. 09/448,641 entitled "Spherical-Shaped Biomedical IC," filed Nov. 24, 1999, and U.S. patent application Ser. No. 09/448,642 entitled "Miniature Spherical-Shaped Semiconductor With Transducer," filed Nov. 24, 1999, which are assigned to the assignee of the present application, and which are incorporated herein by reference.

I. Drug Delivery Modes

Delivery According to Timed Release

In one embodiment, drug delivery is according to a timed release without reliance on physiological parameter sensing. This embodiment is designed for cases where sensing a specific biological marker is either not possible or practical, or when it is determined that programmable boluses released at selectable intervals are sufficient to adequately provide for the patient's needs.

Delivery in Response to Detected Markers

In another embodiment, one or more specific biological markers are detected which then trigger release of the drug(s) based upon internal, preprogrammed logic incorporated in the ball semiconductors causing delivery of a metered dosage of drug to the patient. This system is designed for maintaining therapeutic levels of drugs.

Delivery in Response to Patient Request

In yet another embodiment, drug delivery is based upon a patient request. An external hand-held device triggers the system to deliver a preprogrammed aliquot of drug. This system can be used for relief of temporary pain syndromes which occur postoperatively, relief of intermittent pain syndromes which occur in conditions of angina pectoris, and persistent prolonged pain syndromes which occur with chronic conditions such as malignancies or neuropathies including phantom pain syndrome present following limb amputation. This system provides independent sensing of the drug concentration on the same ball, separate ball, or aggregate of balls. These sensing balls may have control circuitry which includes programming to override the triggering signal to prevent the delivery of the drug, if the drug concentration has reached a programmed threshold level, as prescribed by the physician.

II. Multiple Formats for the Delivery System

Hydrogel Delivery System

In addition to the modes of drug delivery, the disclosed delivery system includes three distinct formats. In the first format, the ball has a polyelectrolyte hydrogel covalently attached to its surface, and the ball is implanted within the body. Most favorably, this implantation is in a small cavity such as the spinal canal, brain, sinuses, eye, middle or inner ear, or within a wound. The attached hydrogel serves as the drug reservoir by trapping the drug within its regions. The polyelectrolyte is designed to collapse down tightly to the surface of the ball semiconductor when the surface of the ball has an electrical charge of the opposite polarity as the polyelectrolyte. This tight binding of the hydrogel reduces the ability of the drug to diffuse through the hydrogel, minimizing drug release. Conversely, when the charge on the ball reverses polarity, the polyelectrolyte is repelled by the surface charge causing the hydrogel to quickly swell (or "blossom") into the aqueous environment, and thereby promoting the release of the drug. In this way, the delivery of the drug is turned on and off with each change in the surface charge. This format of drug delivery is particularly designed for cases where small dosages over short periods are required.

Implantable Capsule having a Self-Contained Reservoir and Accompanying Delivery System The second format is an implantable capsule having a self-contained drug reservoir, and a system of ball semiconductors to act as timers, sensors, motors or actuators (or stimulators) for the controlled release of the drug from the reservoir. This format is typically for larger cavities such as the peritoneal cavity, thoracic cavity, or within the scalp. The reservoir is designed to hold enough medication for several months, after which time the capsule can be surgically removed.

Implanted Reservoir System having Drug Release According to Detection of Physiological Markers The third format is a subcutaneous reservoir and pump mechanism with one or more sensing balls at the same or a remote site. The sensing balls detect specific physiological markers and relay information to the pump mechanism to deliver a metered dosage of the drug based on the measured physiologic parameters.

III. Accompanying Safety Features

Each of the abovementioned modes of drug delivery incorporate numerous safety features. For example, each delivery format may include a set of sensor balls, where possible, that detect the concentration of drugs that are actually released. This sensor system acts as a fail-safe device, and if the released concentration exceeds a physician's programmed threshold level, can turn off the releasing balls, warn the patient, and automatically alert medical professionals. Additionally, a ball semiconductor can be reprogrammed telemetrically, and dysfunctional balls can be turned off. In cases where a fluid reservoir is maintained subcutaneously, the integrity of the reservoir can be easily verified by plotting the pressure-versus-volume relationship each time the reservoir is refilled, or whenever it is believed the system is in need of maintenance. This is accomplished by placing a ball semiconductor on the tip of the needle used to fill the reservoir, which embodiment is described in greater detail hereinbelow. This needle-based ball semiconductor measures hydrostatic pressure within the reservoir, flow through the needle, and has been previously described in the above-referenced patent application entitled "Spherical-Shaped Biomedical IC." This allows for checking the mechanical integrity of the reservoir at each filling session, or anytime compromise is suspected. Due to the flexibility provided by the implementation of ball semiconductors, numerous other safety features may be incorporated to ensure the safe delivery of drugs. For example, where drug delivery is mandatory for survival of the patient, an accidental over-release scenario can be controlled to the extent that drug release can still be provided, but will drop back to a prescribed level according to programmed instructions. Additionally, multiple ball systems may be employed in a parallel implementation to ensure that where one system fails, the other will be operational.

Referring now to FIG. 1, there is illustrated a general block diagram of the circuitry of a ball semiconductor 110 and associated remote control system. In this particular embodiment, a dashed line 138 separates the ball 110 on the right side as deployed within the patient's body from a remote control station 140 on the left side located outside the patient's body. As noted hereinabove, the remote control station 140 need not be located external to the human body, but may be implanted in the body proximate to or remoted from the ball 110. The circuitry of the ball 110 can include one or more transducers such as transducer 126, which can sense a condition within the body, or in any environment in which the sensor is placed. The transducer 126 and other elements of the ball 110 preferably are powered by electrical energy coupled into the ball 110 from a remote source. A power coil 128 is wound around a surface portion of the ball 110 to provide a means for receiving energy from outside the body and providing a power source to the ball 110. A power regulator 130 is connected to the coil 128 and supplies DC power to the transducer 26 and other elements of the ball 110, including a processor 132, a transmitter/receiver 134 and a heater circuit 136. The transmitter 134 generates an electromagnetic communications signal 137, which is preferably in the RF band.

The remote station 140, generally, includes a central processing unit (CPU) 142 that is in communication with and controls a power transmitter 144, an RF receiver 146 and a display panel 147 (in the embodiment where the control station 140 is external to the body). Input and user commands to the CPU 142 can be made by conventional means such as a keyboard or mouse (not shown), as used with a typical personal computer. The power transmitter 144 directs a signal 148 at the patient's body and one or more of the balls 110 implanted therein. The primary function of the signal 148 is to power the ball 110, which preferably is accomplished using low frequency electromagnetic radiation. However, an additional function of the signal 148 is to communicate commands to the circuitry on the ball 110. This is preferably accomplished by modulating a high frequency data signal onto the signal 148 to transmit power as well as coded data streams that include commands. Alternatively, data signals can be time division multiplexed with the power transmission signals.

The power transmitter 144 directs the signal 148 at the one or more balls 110, which responds to the varying magnetic field component of the low frequency power signal to induce a current in the power coil 128. The power regulator 130 then converts the AC current induced in the coil 128 to DC current, which is then regulated to provide a relatively constant DC voltage level to the other elements of the ball 110. The processor 132 includes circuitry for demodulating the signal induced in the power coil 128 to extract the data signal to enable commands to be received and executed. The heater 136 can be implemented using polysilicon resistors (not shown here, but described in greater detail hereinbelow) on the surface of the ball 110, or by other means for generating heat known in the semiconductor art. In one embodiment, the heater 136 serves to control drug delivery by activating a temperature sensitive material, such as a seal, on the surface of the ball 110 or in an adjacent reservoir, to release the drugs upon rupturing of the seal.

Referring now to FIG. 2A, there is illustrated the inhibit operation of a single ball coated with a hydrogel 200 made of polyelectrolytes which are covalently attached to the surface 202 of the ball 110. Ball 110 is illustrated with (+) surface voltage for controlling delivery of a drug (indicated by Δ). Drug delivery is inhibited by collapsing the negatively charged (−) polyelectrolyte hydrogel 200 thereby entrapping the drug 204. Polyelectrolyte gels 200 are polymers with electrically charged side groups such as poly (acrylic acid) (PAAc). At physiologic pH, this polymer is highly negatively charged. Drugs 204 may be loaded into this hydrogel 200 by several mechanisms, including ionic interaction, physical entrapment, or hydrolytically cleavable covalent bonds. The release kinetics will be substantially influenced by the method used in loading the drug 204 into the hydrogel 200. The hydrogel 200 can also be modified by the addition of short hydrophobic domains such as oligomers of poly(methyl methacrylate) (PMMA), as described by Inoue et. al., in Journal of Controlled Release 49: 167–176, 1997, as a means of altering the drug release rate. When the surface 202 of the semiconductor 110 is positively charged, the negative charge on the polyelectrolyte gel 200 is attracted to the surface 202 of the ball 110. This collapses the hydrogel 200 and limits the amount of drug 204 that will be able to freely diffuse out from the hydrogel 200 to the surrounding environment Referring now to FIG. 2B, there is illustrated a ball which has become neutrally or negatively charged. The hydrogel 200 freely swells into the surrounding aqueous phase, and the drug 204 is slowly released into the surrounding tissue space 206. Therefore, by altering the charge imposed on the surface 202 of the ball semiconductor 110, one is able to effectively control the delivery of drugs 204. As the amount of drug able to be loaded into this hydrogel is on the order of nanograms to micrograms, this embodiment is preferentially used in small body cavities such as in the brain, spinal canal, sinuses, eye, the inner or middle ear, or in wound-healing applications.

In a related embodiment, temperature sensitive gels can be attached to the surface of the ball rather than polyelectrolytes. Gels such as poly (N-isopropyl acrylamide) (NIPA) undergo large volume changes with small changes in temperature and pH, therefore, drug delivery can be controlled by heating the ball.

Referring now to FIG. 2C, there is illustrated a graph of the temporal changes in surface charge and expected corresponding changes in drug release. Beginning at an arbitrary first point 208 in the process, a positive surface charge is imposed on the ball 110 resulting in a near total inhibition of drug 204 being delivered from the ball 110 to the surrounding area 206. As the surface voltage drops to a negative value, as indicated at the end of phase 208, the hydrogel 200 blossoms over a certain time period which is determined by the pulse width of the voltage applied to the surface 202 of the ball 110. The blossoming effect does not provide an instantaneous release of all of the drug, as indicated in an initial blossoming region 212, but allows for a gradual increase in the release of the drug based upon blossoming reaction time of the hydrogel 200. When blossoming is near maximum, as indicated in a full blossoming region 214, the maximum release of the drug 204 is realized. As indicated by full blossoming region 214, the entrapped drug 204 is now allowed to flow freely from the ball 110 into the surrounding area 206 at or near the highest possible delivery rate. As mentioned hereinabove, sensors may be provided to monitor the release rate of the drug. Therefore, at the prescribed time, or based upon the amount of drug released, the surface 202 of the ball 110 is again changed to a positive polarity to inhibit drug release, as indicated in a phase 216. Based upon the reaction time of the gel, the rate of release of the drug 204 in the region 215 is decreased to a point of near complete inhibition, until the next point in time required for release of the drug.

Referring now to FIG. 3, there is illustrated a wound-healing application involving severed peripheral nerves for nerve regeneration. In this embodiment, a neurotrophin drug such as NT-3, or nerve growth factor (NGF) is loaded into the hydrogel-coated balls 110. The balls 110 are mounted at the distal end 300 of a conduit 302 of neural prosthesis 306. The periodic release of neurotrophin from the attached balls 110 creates a drug concentration gradient to induce the extension of axons 308 through the conduit 302 to the distal nerve ending 300. This results in improved functional recovery of both sensory and motor nerve functions in these patients.

In another application, the hydrogel-coated ball 110 is loaded with a drug for intraocular delivery. Currently, intraocular drug delivery is difficult due to the presence of a blood/retina barrier, similar to the blood/brain barrier. Therefore, a device that can deliver drugs directly when within the interior of the eye, bypassing the blood/retina barrier, is a potentially valuable clinical asset. Some specific examples may be the delivery of a strong antibiotic/antiviral in the case of eye infections, or agents to arrest or reverse the neovascular proliferation associated with diabetes mellitus-induced retinopathy. Retinal Cytomegalovirus infections require treatment with antiviral agents such as Foscarnet and Ganciclovir, which have systemic side effects. Local drug delivery of these agents substantially reduces the systemic side effects that may occur. Similarly, in yet another application, these hydrogel-coated ball semiconductors 110 may be placed directly on the round or oval window of the ear to release drugs into the middle and inner ear.

Figure 4:
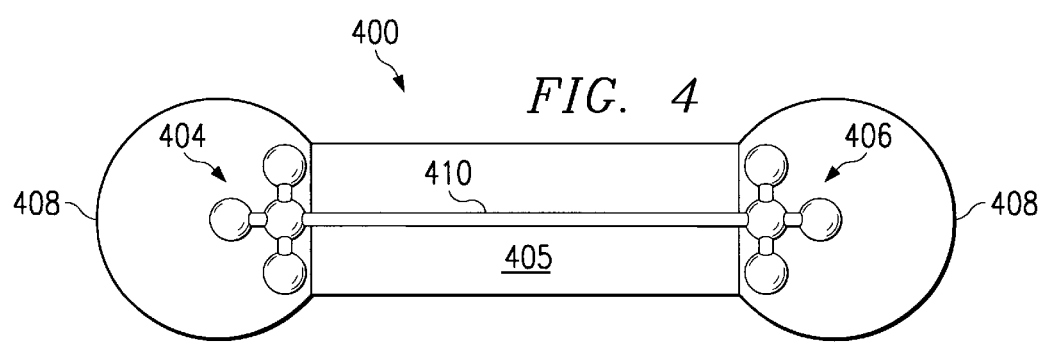
FIG. 4 illustrates a capsule with a reservoir capacity of several month's supply of medication, and the ball system required to sense and direct the delivery of the drugs.

Referring now to FIG. 4, there is illustrated another application in which balls are incorporated within a macroscopic, self-contained device or capsule. Such capsules 400 can contain a reservoir 405 sufficiently large enough for several months of drug delivery after which time the reservoir 405 and associated delivery system can be surgically removed. Depending on the location of placement, these capsules 400 can usually be implanted and retrieved using minimally invasive surgical techniques familiar to those skilled in the art. By way of example, the illustrated capsule 400 has two sets of ball aggregates, a first set 404 for sensing and memory, and a second set 406 implemented for control aspects such as for pumping and dispensing the drug. Notably, the aggregates 404 and 406 may be interconnected by a common bus 410 for communication purposes, or may be implemented to operate independently of each other. Each aggregate 404 and 406 is encased in a semipermeable membrane 408 to allow species which are to be monitored, and drugs to be delivered, to freely diffuse.

Figure 5:
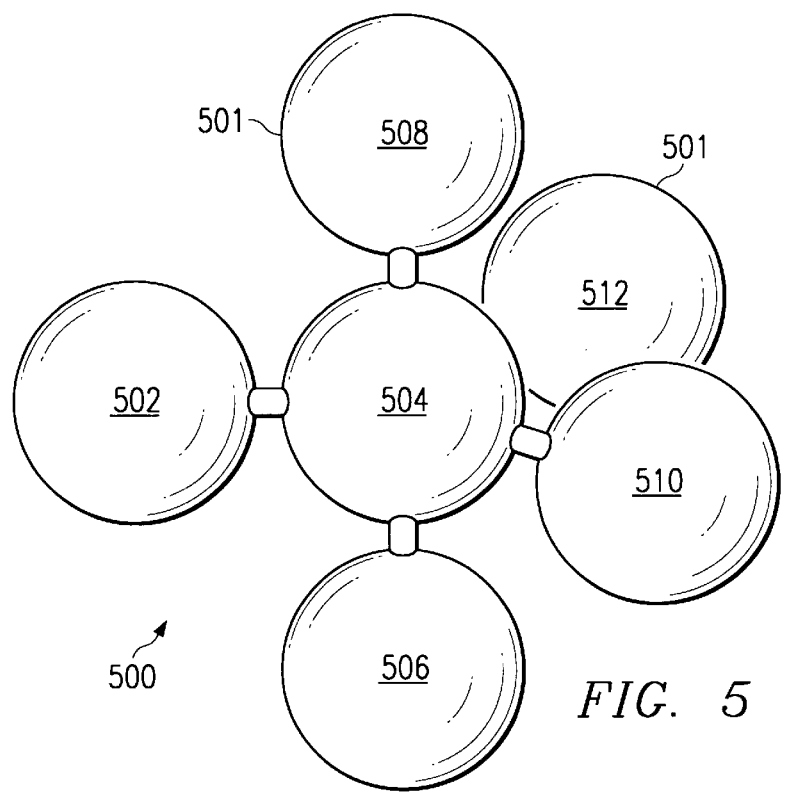
FIG. 5 illustrates a clustered ball aggregation for performing multiple functions.

Referring now to FIG. 5, there is illustrated a clustered ball implementation having multiple functions. In this embodiment, the aggregate 500 of ball semiconductors 501 (similar to ball 110) can serve different functions. For example, one or more sensing circuits on a sensor ball 502 are employed to measure the various desired parameters, a processor ball 504 provides the centralized control and processing function for all aspects of the aggregate 500, a timer ball 506 provides timing to all balls 501 of the aggregate 500 requiring such a signal, an RF communications ball 508 for communicating with external systems, a reservoir ball 510 for measuring fluid reservoir levels, and a memory ball 512 for storing selected parameters such as measured data, program code stored for execution by the processor ball 504, or other conventional uses of such a memory. Notably, some or all of the aforementioned functions may be combined onto one or fewer balls 501. For example, the memory function of the memory ball 512 can be combined onto the processor ball 504 for more speedy access, thereby reducing the size of the aggregate cluster 500 to 5 balls 501. Similarly, the sensing functions of the sensor ball 502 and the reservoir capacity ball 510 (for sensing the current level of drug in the drug reservoir) can be combined onto a single sensing ball, thereby reducing the number of balls 501 in the aggregate cluster 500 to four. These aggregate clusters 500 are designed for placement in larger cavities, such as the peritoneal cavity, the thoracic cavity, or within the skull. Experiments have shown that large-bore chambers made from smooth polyacrylonitrile-poly(vinyl chloride) (PAN-PVC) with an approximate 4.8 mm diameter result in very little fibrosis, abscess formation, or adhesions when implanted in laboratory rat peritoneum, whereas smaller diameter chambers illicit severe reactions (see Lanza et. al., Principles of Tissue Engineering, 1997).

One application of aggregate cluster 500 involves placement within the skull for the treatment of brain tumors. Brain tumors are usually fatal due to the inability to locally excise or deliver chemotherapy to the tumor. The blood/brain barrier makes blood-borne treatment routes difficult and ineffective, and surgical access is limited. Therefore, a drug delivery mechanism that is capable of delivering chemotherapeutic drugs directly to the brain is particularly attractive. In this application, drugs such as BCNU can be delivered directly to the tumor site in a regulated manner over a period of several months. This treatment modality may help reduce the untoward systemic side effects often associated with chemotherapy, and increase the effectiveness of the treatment by increasing the concentration of the drug delivered to the site of interest.

In another application, the hydrogel-coated ball 110 is loaded with anti-epileptic drugs or other movement disorder, mood changing, or cognitive enhancing drugs in the brain in minuscule amounts, but at sufficient concentrations to treat the condition locally without the systemic side effects.

In still another application, the disclosed drug delivery system can be used for the treatment of intractable infections. This can be accomplished by implanting ball clusters 500 within the peritoneal cavity or other suitable body space for the release of strong antibiotics. Often, as is the case with fungal (Candidal) or severe microbial (coagulase-positive Staphylococcal) peritoneal infections involving patients undergoing peritoneal dialysis, the peritoneal dialysis catheters have to be surgically removed due to the inability to eradicate the infection. Morbidity is increased as the patient's renal replacement therapy must be converted to hemodialysis in order to maintain life. Not infrequently, failure to eradicate the infection results in the patient's demise. The inability to cure the patient's infection resides in the inadequacy of conventional drug delivery systems to deliver drugs to isolated areas of the peritoneal cavity. The disclosed delivery system and method allows for localized delivery of higher concentrations of antibiotics to cure the infection without undue systemic toxicity. This treatment modality substantially reduces hospitalization time, cost of health care delivery, and overall morbidity. Such disclosed ball clusters 500 have application whenever short-term drug delivery is required.

Figure 6:
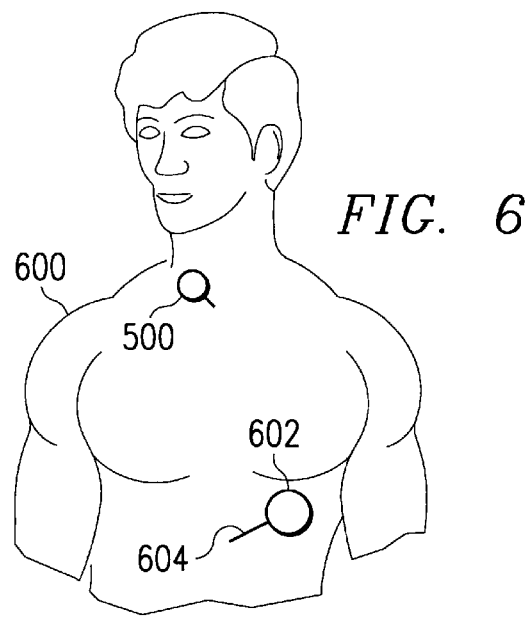
FIG. 6 illustrates an aggregate of balls and a drug reservoir which are implanted within the human body at locations that are the most physiologically relevant to the particular application.

Referring now to FIG. 6, there is illustrated an aggregate of balls and a drug reservoir which are implanted within the human body at locations that are the most physiologically relevant to the particular application. For example, an aggregation 500 of balls is placed within the human body 600 a distance away from a drug reservoir 602 (similar to drug reservoir 405) having a catheter 604 connected thereto. The fluid reservoir 602, having an associated number of balls 501 (oriented similar to aggregates 404 and 406 of FIG. 4) is implanted subcutaneously at an appropriate location for delivery of the drugs or fluids to the site which is distally located from the reservoir 602. Upon delivery of the drug(s), the ball cluster 500 measures the resultant effects at the location of the cluster 500. For example, the ball cluster 500 can be placed near a vessel to measure blood parameters which provide an indication of the effectiveness of the drug upon the desired condition. If blood provides the mechanism by which the curative effects of the delivered dosage levels can be determined, then the measured parameters will determine if the ball cluster 500 is to increase or decrease the amount of drug(s) delivered to the infected site. Similarly, the ball cluster 500 can be implanted near other organs or luminal ducts to measure the effectiveness of the delivered drug(s), such as the urinary tract to measure parameters in the urine while controlling the amount of drug delivered to the infected site. The disclosed architecture essentially provides an implanted system having a control loop with feedback using the measured output parameters.

In operation, a ball semiconductor 501, as either a part of a control aggregate cluster 404 or standing independently at the reservoir 602, receives a signal from the remote sensing balls associated with the aggregate cluster 500 and delivers corresponding information to a system of valves and pumps at the reservoir for controlling drug delivery. The release time is then controlled based upon a followup command from the remote aggregate 500, or even from the measured output at the reservoir. The valves and pumps may be made from ball semiconductors or other micromachines familiar to those skilled in the art. The aggregate 500, based upon signals received from onboard sensors, transmits a signal to the reservoir system to release an aliquot of drug through the catheter 604. This particular configuration is designed for maintenance or long-term periods of drug delivery for the treatment of chronic illnesses, such as delivery of insulin to diabetic patients; delivery of anticonvulsants to epileptic patients; delivery of drugs to treat movement disorders such as Parkinson's disease; cardiovascular drugs to treat coronary artery disease, cardiac arrhythmias, hypertension, and cardiomyopathies; anticoagulants to treat hypercoagulable states or maintain anticoagulation in patients with prosthetic heart valves; immunosuppressive medications to treat autoimmune disorders or organ transplant patients; and anti-inflammatory medications to treat degenerative arthritic conditions. The disclosed system has the advantage of ensuring patient compliance by providing the capability of removing patient interaction from system operation, thereby ensuring that a therapeutic level is maintained at all times. Bioavailability is much less of a problem as absorption through the gastrointestinal tract is not required.

Figure 7:
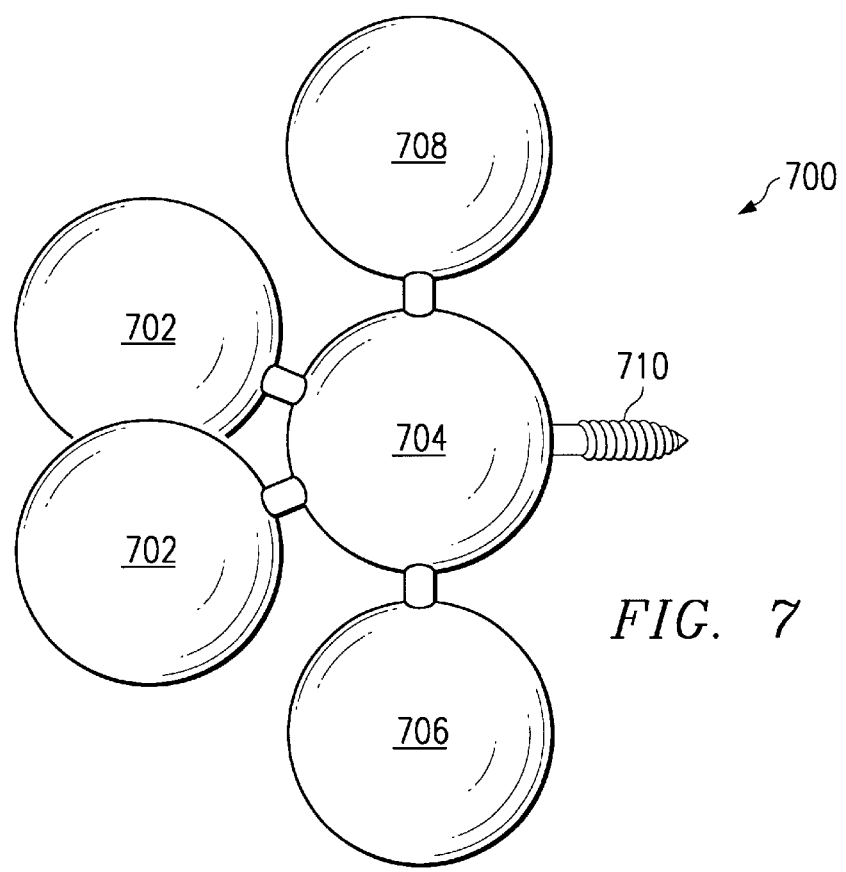
FIG. 7 illustrates a ball aggregation using a tissue screw for attachment to tissue.

Referring now to FIG. 7, there is illustrated a ball aggregation using a tissue screw for attachment to tissue. The ball aggregation 700 (similar to aggregation 500) includes one or more sensor balls 702, a processor ball 704, a timer ball 706, which under control of the processor ball 704, or independently, periodically instructs the sensor balls 702 to take measurements, and then relay those measurements to a transmitter ball 708 under the control of the processor ball 704. The transmitter ball 708 is dedicated to communicating with the sensor balls 702 and other balls located at the reservoir 602, as well as receiving power and RF communications from outside the body 600. The processor ball 704 is programmed to direct operations of the aggregate cluster 700 and communicate with the other balls in the cluster 700. In this particular embodiment, a mechanical screw mechanism 710 is used to attach the ball cluster 700 to surrounding tissue. This is but only one way of securing the implanted system. Another method of securing the ball cluster can be through the use of tissue glues, recognizing that the glue must not inhibit the functionality or operability of the drug delivery system by covering any sensors or other necessary interfaces to the desired medium which are to be measured.

In another application, an external hand-held device triggers the release of one or more drugs at the patient's request. The patient requests a dose of drug using a hand-held device. This signal transmits power and information to the implanted drug delivery system. When this signal is received by the transmission ball, it relays the signal to the central processing ball. The central processing ball then queries the sensors where drug concentration is measured and this information is relayed back to the central processing ball. The central processing ball stores information regarding the times and amounts of drug already dispensed to the patient. It then makes the decision based on the amount of drug currently measured in the system, and the dosage limit for the particular patient if, and how much drug should be administered. If drug is to be dispensed to the patient, this information is then transmitted to the dispensing balls. This embodiment may employ either the capsule or subcutaneous reservoir format of drug delivery depending upon physician's opinion on the duration of patient's need. This delivery system is designed for relief of pain from such sources as: angina pectoris, post-operative pain, or chronic pain syndromes. It may also have application to epileptic patients where the hand-held device is given to family members or caregivers to help arrest severe seizures.

In a variation of this embodiment, a safety system is installed consisting of several sensor ball clusters that are capable of sensing the drug being released. If more than one of the sensing ball aggregates detect that the drug concentration has exceeded a level pre-programmed by the physician, and which may detrimental to the patient's health, the sensing balls shut down drug delivery to prevent accidental or intentional overdose. In a further implementation, where complete denial of the drug would be detrimental to the patient, the safety system could be programmed to execute a backup program or a shutdown algorithm which overrides all systems in order to attempt to moderate the delivery of drugs through a second backup ball cluster while signaling a remote system to notify the patient, doctor or medical personnel for immediate attention. A safety feature for checking the integrity of fluid flow is described in pending and commonly-assigned U.S. patent applications: Ser. No. 09/448,678 entitled "Monitor for Interventional Procedures," and Ser. No. 09/448,641 "Intraluminal Monitoring System," both of which are incorporated herein by reference.

Figure 8:
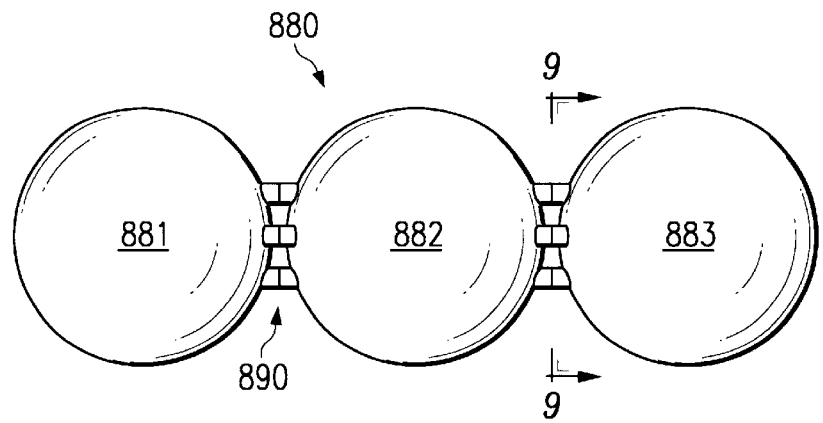
FIG. 8 illustrates a side elevation of a cluster of semiconductor balls that may be employed in a transducer function.

Referring now to FIG. 8, there is illustrated a side elevation of a cluster 880 of semiconductor balls that may be employed in a sensor function, according to a disclosed embodiment. Although a single ball can include the foregoing functions, more complex monitoring functions with multiple sensors (or transducers) can be implemented using multiple ball systems attached to catheters, needles and other insertable devices. For example, the cluster 880 can include a ball 881 for power receiving and data transmission functions. Alternatively, ball 881 can be a miniature battery. A ball 882 can include a first transducer function, such as pressure sensing, and a ball 883 can include a second transducer function, such as measuring pH, $PO_2$, $pCO_2$, or temperature, as the particular application requires. Connections between the balls are made through metal contacts 890, which may be solder bumps.

Figure 9:
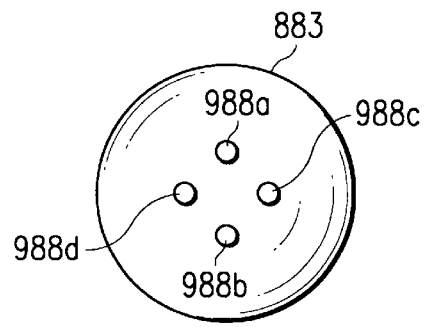
FIG. 9 illustrates a cross section along a line 9—9 to expose electrical contacts between two connected balls.

Referring now to FIG. 9, there is illustrated a cross section taken along the line 9—9 of FIG. 8 to expose the four contacts 988a, 988b, 988c and 988d between ball 882 and ball 883. The contacts 988a and 988b may be power contacts, such as a positive 3.0 volts and ground, which can be passed from ball 881 around ball 882 by conductors on its surface using two of a group of similar contacts (designated collectively by numeral 890 in FIG. 8). The contacts 988c and 988d may be data and control contacts for communications between ball 882 and ball 883. Similarly, data and control contacts may exist among contact group 890 between ball 881 and ball 882 to the extent needed.

Figure 10:
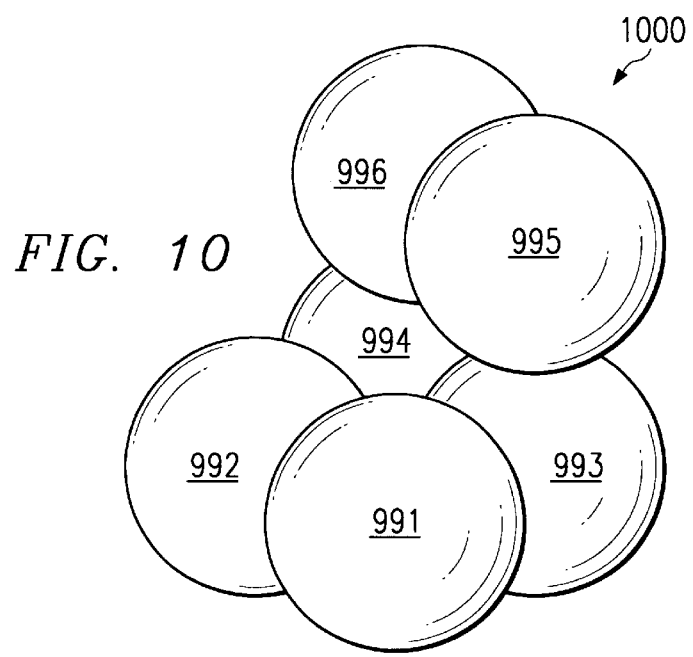
FIG. 10 illustrates a schematic depiction of a cluster of semiconductor balls that have application in the context of a disclosed embodiment.

Referring now to FIG. 10, there is illustrated a cluster or aggregation 1000 of balls 991, 992, 993, 994, 995 and 996, as an example of the versatility of such ball systems. The cluster 1000 specifically shows six balls arranged in a three-dimensional configuration. It will be appreciated that various other cluster arrangements are possible, limited only by the constraints of the end-use application. Each of the balls of the cluster 1000 can perform different electronic functions and communicate with each other through contacts as described above in connection with FIGS. 8 and 9. For example, ball sensors can be located on the sides of catheters to measure various parameters. Clustered balls are able to integrate, transmit, and receive more complex information or actuate a response (emit laser, infrared, ultrasound, or electrical energy). The actuators may contain a piezoelectric driver attached to a ball surface for ultrasound generation and control for measurements of luminal diameter and fluid flow rate within the vessel lumen. Such actuators can serve as an emitting device allowing for external detection to determine location or position.

Figure 11:
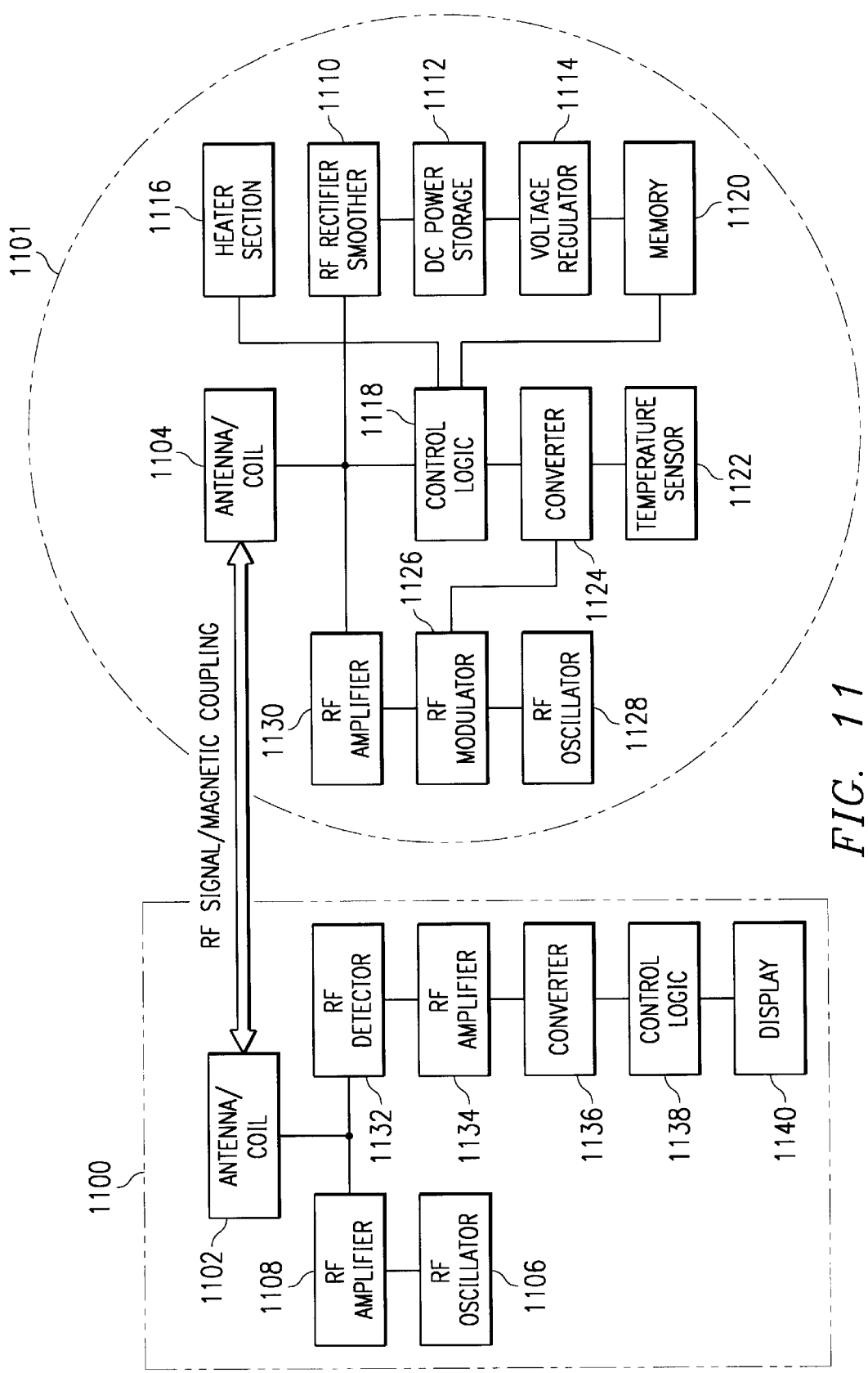
FIG. 11 illustrates a more detailed block diagram of a remote control system and a ball having heating and temperature-sensing capabilities.

Referring now to FIG. 11, there is illustrated a more detailed block diagram of an external control system and a ball having heating and temperature-sensing capabilities. A control system 1100 (similar to control system 140) includes an antenna/coil 1102 that transmits RF power to an antenna/coil 1104 of a ball 1101 (similar to balls 501 and 110). Power is transported either by RF radiation or by magnetic coupling between the control system antenna/coil 1102 and the ball antenna/coil 1104. Control system 1100 generates RF power with an RF oscillator 1106 coupled to an RF amplifier 1108. The RF amplifier 1108 is coupled to the control system antenna/coil 1102. RF power received at antenna/coil 1104 of ball 1101 is rectified and smoothed by an RF rectifier/smoother 1110 coupled to the antenna/coil 1104. The RF rectifier/smoother 1110 converts RF energy to a DC voltage. The DC power is stored in a DC power storage unit 1112, which may be a capacitor, a battery, or the combination thereof. The capacitor of the DC power storage unit 1112 may be included in the smoothing portion of RF rectifier/smoother 1110. A voltage regulator 1114 is coupled to the DC power storage unit 1112 to regulate the DC voltage in order to provide stable voltage for powering the ball 1101, for any condition or distance between control system 1100 and the ball 1101. The voltage regulator 1114 supplies DC voltage to all circuits of ball 1101, in a manner well-known to those skilled in the art.

A heater section 1116 is controlled through a control logic section 1118 (similar in operation to the microprocessor 132), which switches power from the antenna/coil 1104 through to the heater section 1116 according to either received or programmed commands. The switching function is illustrated as part of the control logic 1118. The control logic 1118 may be configured to control the activity of all the circuits on ball 1101. The control logic 1101 may be a microcontroller, a digital signal processor, or any other processor suitable to the size constraints and functions required to be processed. The control logic 1118 interfaces to a memory 1120 for storing information, and reading information therefrom on command from the control system 1100, or perhaps according to an algorithm running in the control logic 1118. One or more temperature sensors 1122 (similar in operation to the transducer 126) measure the temperatures associated with the heater section 1116, which heater section 1116 may comprise one or more heating elements fabricated at various locations on the thermal-sensing ball 1101, as determined by the particular application. The output of the temperature sensor 1122 is converted to digital data via an A/D converter 1124. The converter 1124 is controlled by the control logic 1118, and connects to an RF modulator 1126 for modulation of the digital data onto an RF carrier signal generated by an RF oscillator 1128 for transmission from the ball 1101. The modulated signal from the RF modulator 1126 is amplified using an RF amplifier 1130 to obtain sufficient signal strength for coupling from the ball 1101 to the control system 1100.

The frequency of RF oscillator 1128 is preferably not the same as the frequency generated by RF oscillator 1106 of control system 1100. The RF signal produced by RF oscillator 1128 is modulated with the signal produced by converter 1124 in the RF modulator 1126. The ball 1101 may operate under AM, FM, PM, or any other analog and digital modulation methods. The information transmitted from the ball 1101 is received at the control system antenna/coil 1102. The received RF signal is detected by an RF detector 1132 and amplified by an RF amplifier 1134. The amplified signal is converted to a digital signal by an A/D converter 1136. The converter 1136 is coupled to control logic 1138 (similar to the control functions provided by the CPU 112 and control logic 1118), which processes the data received from ball 1101, and controls a display 1140 and other electrical circuitry of control system 1100. The display 1140 provides audio and visual signaling to a human operator, with the visual aspect being as simple as an LED, or as complex as a computer display, or it may simply be an interface to other instrumentation equipment.

Notably, the remote system may actually be external to the human body, or may be implanted in the human body a short distance from the reservoir system, or proximate to the reservoir system. Furthermore, the reservoir system and the control system may be consolidated into a single assembly such that the reservoir system operates solely from its own embedded power source (e.g., a battery ball system). Alternatively, the consolidated and implanted reservoir/control system receives power and communications from yet another external control system that works cooperatively with the implanted reservoir/control system. It is also conceivable that a network of implanted reservoir/control systems can be implemented to substantially simultaneously deliver a drug at various selected sites in the human body, or perhaps deliver a series of different drugs which having a cooperative effect at respective locations throughout the body. The synchronized release (or even staggered release) can then be controlled by nearly simultaneous communication with the implanted reservoir/control systems to facilitate the desired release rates and parameters. Where a network of ball aggregates is employed, preferably communication to each aggregate is accomplished with a unique frequency to ensure unimpeded communication of the desired commands to respective aggregates.

Figure 12:
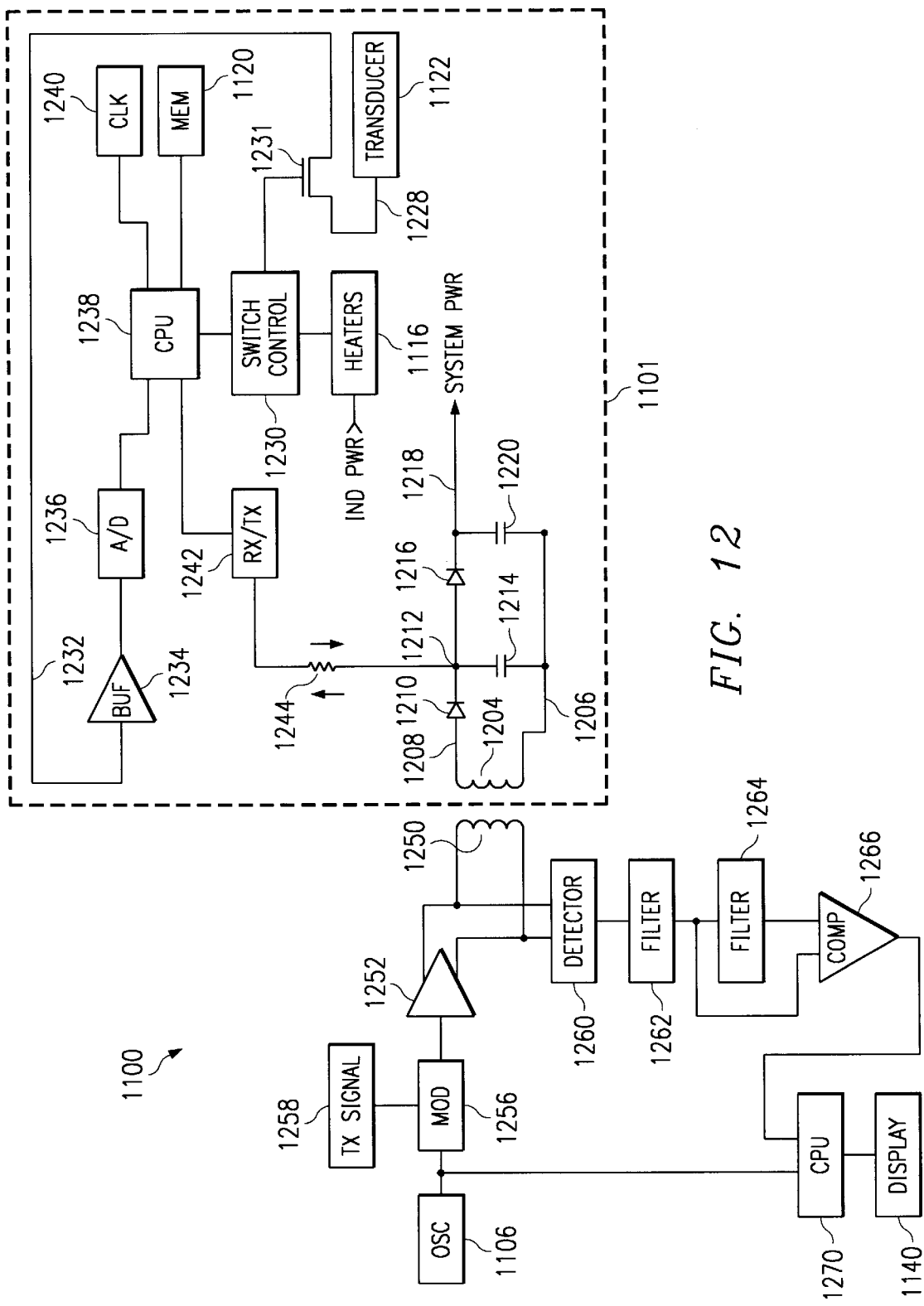
FIG. 12 illustrates a schematic block diagram of the monitoring station and thermal-sensing ball of FIG. 11.

Referring now to FIG. 12, there is illustrated a schematic block diagram of the embodiment of the monitoring station and thermal-sensing ball of FIG. 11. The ball 1101, as described hereinabove, is operable to provide a transducer 1122 for interfacing with the desired quantitative condition, in this particular discussion, temperature. The illustrated embodiment is that associated with a "passive" system, which term refers to a system having no battery associated therewith. In order to operate the system, there is provided an inductive coupling element 1204 in the form of an inductor, which is operable to pick up an alternating wave or impulse via inductive coupling, and extract the energy therein for storage in the inductive element 1204. This will create a voltage across the inductive element 1204 between a node 1206 and a node 1208. A diode 1210 is connected between the node 1208 and the node 1212, with the anode of diode 1210 connected to node 1208 and the cathode of diode 1210 connected to a node 1212. Typically, the diode 1210 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 1210 is operable to rectify the voltage across the inductive element 1204 onto the node 1212, which has a capacitor 1214 disposed between node 1212 and node 1206. Node 1212 is also connected through a diode 1216 having the anode thereof connected to node 1212 and the cathode thereof connected to a node 1218 to charge up a capacitor 1220 disposed between node 1218 and 1206. The capacitor 1220 is the power supply capacitor for providing power to the ball 1101. The capacitor 1214, as will be described hereinbelow, is operable to be discharged during operation of the system and, therefore, a separate capacitor, the capacitor 1220, is required for storing power to power the system of the ball 1101.

There is also provided a switching transistor 1231 which has one side of the gate/source path thereof connected to a node 1228 which is the output of the transducer 1122, and the other side thereof connected to a node 1232. The gate of transistor 1231 is connected to the output of a switch control 1230. Node 1232 is connected to the input of a buffer 1234 to generate an analog signal output thereof which is then converted with an analog-to-digital converter 1236 to a digital value for input to a CPU 1238. The CPU 1238 is operable to receive and process this digital input voltage. A clock circuit 1240 is used for providing timing to the system. The memory 1120 is provided in communication with the CPU 1238 to allow the CPU 1238 to store data therein for later transmittal back to the control system 1100 or for even storing received instructions. This memory 1120 can be volatile or it can be non-volatile, such as a ROM. For the volatile configuration, of course, this will lose all information when power is removed. The CPU 1238 is operable to provide control signals to the switch control 1230 for turning on the transistor 1231 at the appropriate time. In addition to the transistor 1231 being toggled to read the transducer 1122, transistor 1231 could be a pass-through circuit such that the CPU 1238 can continually monitor the voltage at the output of the transducer 1122. The CPU 1238 also controls the flow of power to one or more heater sections 1116 through the switch control 1230. System power to all power-consuming elements of the ball 1101 is provided at the SYSTEM PWR output (or node 1218).

The memory 1120, in conjunction with the operation of the CPU 1238, can be operated such that a temperature history can be stored for the one or more internal temperature sensors 1122. For example, if the reservoir system having the transducer 1122 were implanted, a temperature history could be recorded continuously, or at set times. Similarly, the temperature profile could be stored and uploaded to the control system 1100 for immediate or later analysis. This would require a time base, which is provided by RF oscillator 1128 (illustrated herein as part of a transmit/receive circuit 1242) and which would comprise an integral part of the operation of the CPU 1238. This allows information in the form of temperature measurements to be taken at certain times. In one embodiment, once the transducer 1122 is removed from the body, it can then be "scanned" and the information stored therein downloaded. Further, this temperature information may only be stored temporarily until a download operation, at which time the memory 1120 is cleared and new data is taken. This would allow the memory 1120, which may be limited in capacity, to be cleared periodically.

In order to communicate with the CPU 1238 for transferring data thereto and for allowing the CPU 1238 to transfer data therefrom, the receive/transmit circuit 1242 is provided for interfacing to node 1212 through a resistive element 1244. This allows RF energy to be transmitted to node 1212. It is important to note that the semiconductor junction across diode 1210 is a capacitive junction. Therefore, this will allow coupling from node 1212 to node 1208. Although not illustrated, this could actually be a tuned circuit, by selecting the value of the capacitance inherent in the design of the diode 1210. In any event, this allows an RF connection to be provided across diode 1210 while allowing sufficient energy to be input across inductive element 1204 to provide a voltage thereacross for rectification by the diode 1210 and capacitor 1214. Typically, the frequency of this connection will be in the MHz range, depending upon the design. However, many designs could be utilized. Some of these are illustrated in Beigel, U.S. Pat. No. 4,333,0112, entitled "Identification Device," issued Jun. 1, 1982, and Mogi et al., U.S. Pat. No. 3,944,982, entitled "Remote Control System For Electric Apparatus," issued Mar. 16, 1976, which are incorporated herein by reference. With these types of systems, power can continually be provided to the node 1212 and subsequently to capacitor 1220 to allow power to be constantly applied to the ball 1101. Note that as mentioned hereinabove, the functions illustrated in this particular drawing could also be separated such that, e.g., the transducer and heater sections are designed into independent balls.

The control system 1100 which can either be disposed outside of the body and proximate to the ball 1101, or implanted in the body a short distance from the reservoir system 400, or proximate to the reservoir system 400, includes an inductive element 1250 for coupling power and/or communication to and from the ball 1101. The inductive element 1250 is driven by a driving circuit 1252 which provides a differential output that is driven by an oscillator 1106. This will be at a predetermined frequency and power level necessary to couple energy from inductive element 1250 to inductive element 1204. Since this is an external system, the power of the oscillator can be set to a level to account for any losses through the body tissues. To allow information to be transmitted, a modulation circuit 1256 is provided which is modulated by a transmitter signal in a block 1258 that allows information to be modulated onto the oscillator signal of the oscillator 1106, which oscillator signal is essentially a "carrier" signal. However, it should be understood that the information that is transmitted to the ball 1101 could merely be data information, whereas the CPU 1238 could operate independent of any transmitted information to provide the temperature output. Alternatively, entire control of the ball system 1101 could be provided by the transmit signal 1258 and the information carried thereon, since power must be delivered to the illustrated embodiment due to the lack of any independent power in the ball 1101.

When the information is received from the ball 1101, it is superimposed upon the oscillator signal driving the inductive element 1250. This is extracted therefrom via a detector 1260 which has the output thereof input to a first low pass filter 1262, and then to a second low pass filter 1264. The output of low pass filters 1262 and 1264 are compared using a comparator 1266 to provide the data. The filter 1262 provides an average voltage output, whereas the filter 1264 provides the actual digital voltage output. The output of the comparator 1266 is then input to a CPU 1270 which also is powered by the oscillator 1106 to process the data received therefrom. This can then be input to a display 1140.

Figure 13A:
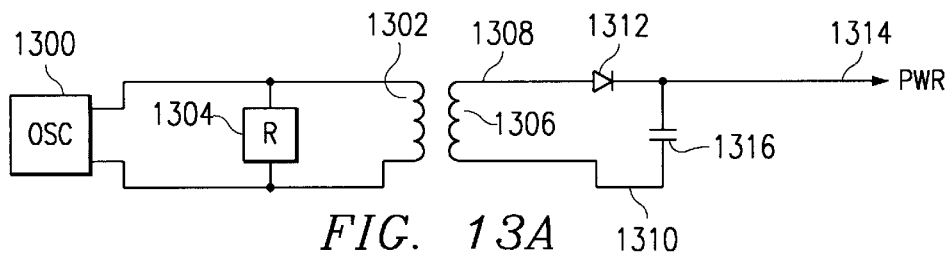
FIGS. 13A–C illustrate alternate embodiments for the transmit/receive operation.
Figure 13B:
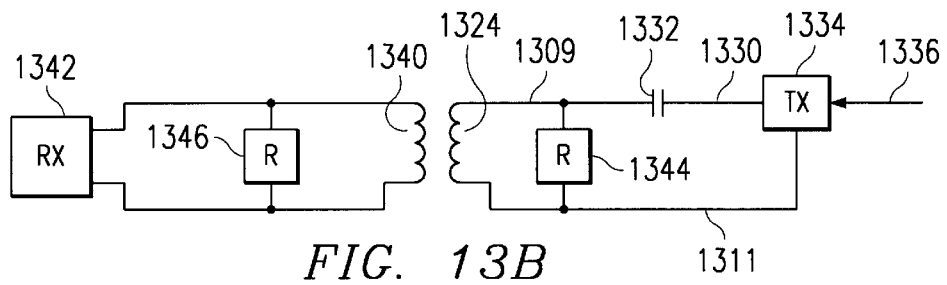
Figure 13C:
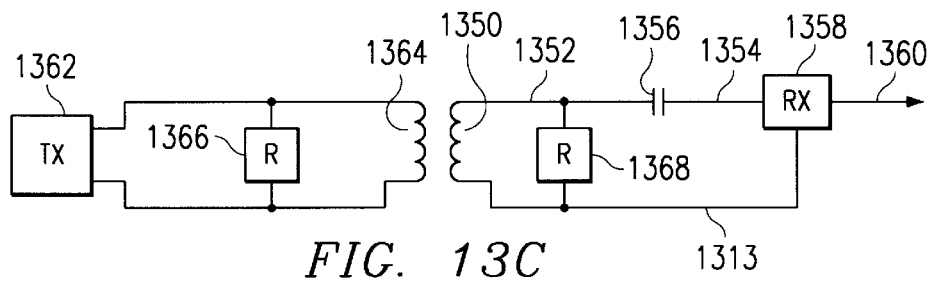

Referring now to FIGS. 13A–C, there are illustrated alternate embodiments for the transmit/receive operation. In FIG. 13A, there is provided an oscillator 1300 which drives an inductive element 1302. Typically, there is some type of load 1304 disposed across the inductive element 1302. This is the primary power that is provided to the system. A separate inductive element 1306 is provided on the ball 1101, for being inductively coupled to the inductive element 1302. Thereafter, a voltage is generated across the inductive element 1306, the inductive element 1306 being connected between nodes 1308 and 1310. A diode 1312 is connected between node 1308 and a power node 1314, and a power supply capacitor 1316 is disposed across node 1314 and a node 1310. This allows the voltage on node 1308 to be rectified with diode 1312.

In FIG. 13B, the receive operation, in this alternative embodiment, utilizes a separate inductive element or antenna 1324 in the ball 1101, which is operable to be connected between nodes 1309 and 1311. Node 1309 is capacitively coupled to a transmit node 1330 with a capacitor 1332, the capacitor 1332 being a coupling capacitor. A transmitter 1334 is provided for transmitting received data from a line 1336 to the node 1330, which is then coupled to the node 1309 to impress the RF signal across the inductive element 1324. A corresponding inductive element 1340 is disposed on the remote controller of control system 1100, which inductive element 1340 is operable to be disposed proximate to the inductive element 1324, or a distance therefrom depending upon the signal power. The inductive element 1340 is basically a "pick-up" element which is operable to receive information and function as an antenna, and provide the received signal to a receiver 1342. The structure of FIG. 13B is a separate structure, such that node 1309 is isolated from node 1308, the power receiving node. However, it should be understood that any harmonics of the oscillator 1300 would, of course, leak over into the inductive element 1324. This can be tuned out with the use of some type of tuning element 1344 on the ball 1101 disposed across inductive element 1324, and also a tuning element 1346 disposed across the inductive element 1340, i.e., the antenna.

Referring now to FIG. 13C, there is illustrated a simplified schematic diagram of the receive portion. The ball 1101 has associated therewith a separate receive antenna or inductive element 1350 disposed between node 1313 and a node 1352. Node 1352 is capacitively coupled to a receive node 1354 with a coupling capacitor 1356. A receiver 1358 is provided for receiving the information transmitted thereto and providing on the output thereof data on a data line 1360. The receiver 1358 is operable to receive the RF signal, demodulate the data therefrom, and provide digital data on the output 1360. A transmitter 1362 is operable to impress a signal across an external inductive element 1364. The inductive element 1364 basically provides the RF energy and is essentially tuned with a tuning element 1366. A corresponding tuning element 1368 is provided on the ball 1101 and disposed across inductive element 1350, the inductive element 1350 acting as an antenna, as well as the inductive element 1364.

Note that in circumstances where the signals of ball 1101 cannot be adequately received therefrom and/or power coupled thereto, the signal coupling head of the control system 1100 may need to be placed proximate to the ball 1101 in order to couple the transmit/receive signals and power. Furthermore, where more than one ball 1101 is used, as in the aforementioned aggregate clusters (500, 700, and 1000) communication of power and data signals between the various ball 1101 may need to employ distinct time periods (i.e., time multiplexing) when communication occurs using a single common frequency, or discrimination circuits may need to be used where communication occurs simultaneously with the plurality of implanted balls 1101 having different oscillator frequencies.

Figure 14:
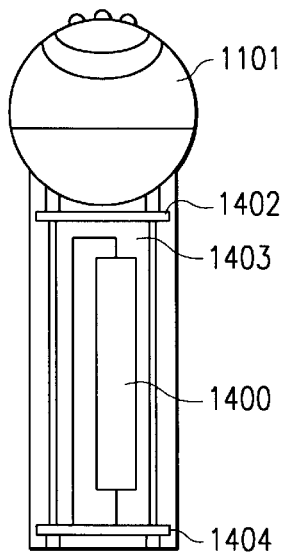
FIG. 14 illustrates a side view of an alternative embodiment utilizing additional circuitry or structure attached to the ball for providing a local power source.

Referring now to FIG. 14, there is illustrated a side view of an alternative embodiment utilizing additional circuitry or structure attached to the ball 1101 for providing a local power source. As described hereinabove, the ball 1101 requires a power-generating structure for storing a power supply voltage such that diodes must be provided for receiving and rectifying a large amount of power and charging up a power supply capacitor. Alternatively, the ball 1101 could be configured to interface to an attached power supply system 1400 comprising either a battery or a capacitor, or both. The local power supply system 1400 is illustrated as disposed on a circuit board 1403 defined by supporting structures 1402 and 1404. The circuit board 1403 contains electronics for interfacing the local power supply system 1400 to the ball 1101. The entire structure of FIG. 14 would be encapsulated, with only a thin layer thereof disposed over ball 1101.

Figure 15:
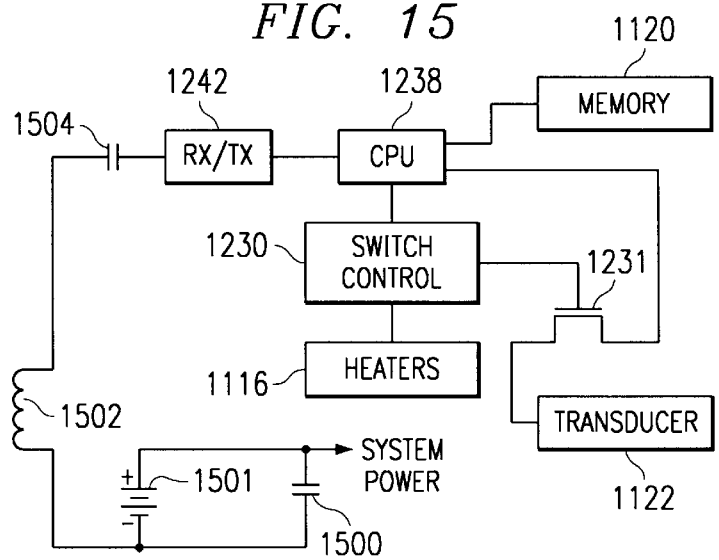
FIG. 15 illustrates a schematic block diagram of the ball using a battery as the local power supply system.

Referring now to FIG. 15, there is illustrated a block diagram of the ball 1101 using a battery as the local power supply system. A battery 1501 is provided as a source of self-contained power and is connected across a capacitor 1500 to providing smoothing of any power output to the system power-consuming elements of the ball 1101. Power for all on-board components is obtained from the SYSTEM POWER output by providing sufficient charge to the capacitor 1500. The capacitor 1500 could be formed on the surface of the ball 1101 or it could actually be part of the battery structure 1501. Additionally, the capacitor 1500 could actually be the capacitance of the battery 1501. Additional structure could be provided for powering the CPU 1238 and the other circuitry on the ball 1101 from the battery 1501. As such, there would only be required a smaller inductive element 1502 and a capacitor 1504 to allow the receive/transmit block 1242 to receive/transmit information from and to the control system 1100. The switch control 1230 controls the gate of the switching transistor 1231 to switch the output of the transducer 1122 through the switching transistor 1231 source/drain path to the CPU 1238. The CPU 1238 switches received power through the switch control 1230 to one or more heaters 1116 on the ball 1101. The memory 1120 contains stored information which, for example could be a unique ID, and perhaps patient and physician information, drug information, etc.

Figure 16:
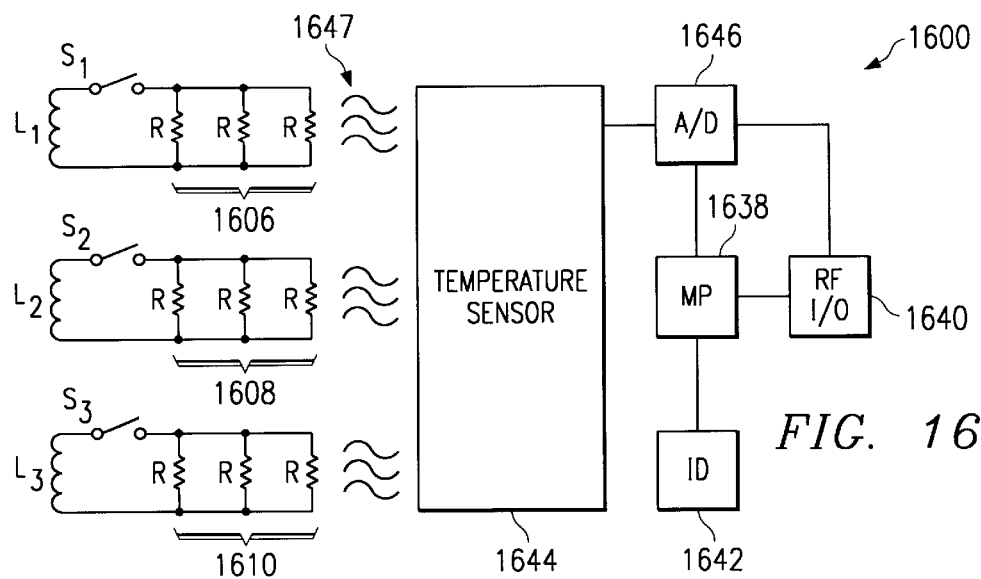
FIG. 16 illustrates a general circuit block diagram of the thermal-sensing ball with emphasis on the heater sections.

Referring now to FIG. 16, there is illustrated a general circuit block diagram of the thermal-sensing ball with emphasis on the heater sections. The circuit 1600 includes a microprocessor (MP) 1638 that controls all functions of the thermal-sensing ball 1101. The circuitry of each thermal-sensing ball 1101 is powered by an RF circuit which is part of an input/output (I/O) circuit 1640. Each thermal-sensing ball 1101 includes its own unique identification serial number (ID) stored in an ID memory 1642. The heat generated on the ball 1101 is measured by a temperature sensor 1644 (similar to transducers 126 and 1122), which provides analog temperature information to an analog-to-digital converter (A/D) 1646 (similar to converters 1124 and 1236). Alternatively, analog temperature data can be modulated onto an RF carrier frequency and transmitted by the RF input/output (I/O) circuit 1640. Since it is useful to transmit digital ID information from ID memory 1642 along with the temperature data, it is preferable to convert the temperature data to digital form using the A/D converter 1646. The structure of the temperature sensor 1644 may be a circuit containing a large-area diode whose forward current is calibrated to measure temperatures in a narrow range. It is well known that a slightly forward-biased PN junction has a temperature-dependent forward current. As will be mentioned hereinbelow, the temperature-sensing operation may also be performed using a band gap reference circuit.

Thermal energy 1647 is generated on the thermal-sensing ball 1101 by way of coupling energy signals to receiving coils $L_1$, $L_2$ and $L_3$, each of which couples transmitted energy from the control system 1100 into one or more sets (1606, 1608, and 1610) of resistive heater elements R. The heater elements R can be implemented as resistive polycrystalline strips on the surface of each thermal-sensing ball 1101, as will be discussed in greater detail hereinbelow. The coils $L_1$, $L_2$, and $L_3$ are preferably arranged in mutually orthogonal planes so that the thermal-sensing ball 1101 receives RF energy regardless of its orientation in the human body. Power to the heater elements R is switched by respective switches $S_1$, $S_2$, and $S_3$, of the coils $L_1$, $L_2$, and $L_3$. The switches $S_1$, $S_2$, and $S_3$ are implemented as transistors which are controlled by the microprocessor 1638, and can be opened to selectively disable the resistive heating elements R. This feature allows heat generation to be remotely controlled by the control system 1100 to more effectively deliver the desired heat levels.

Figure 17:
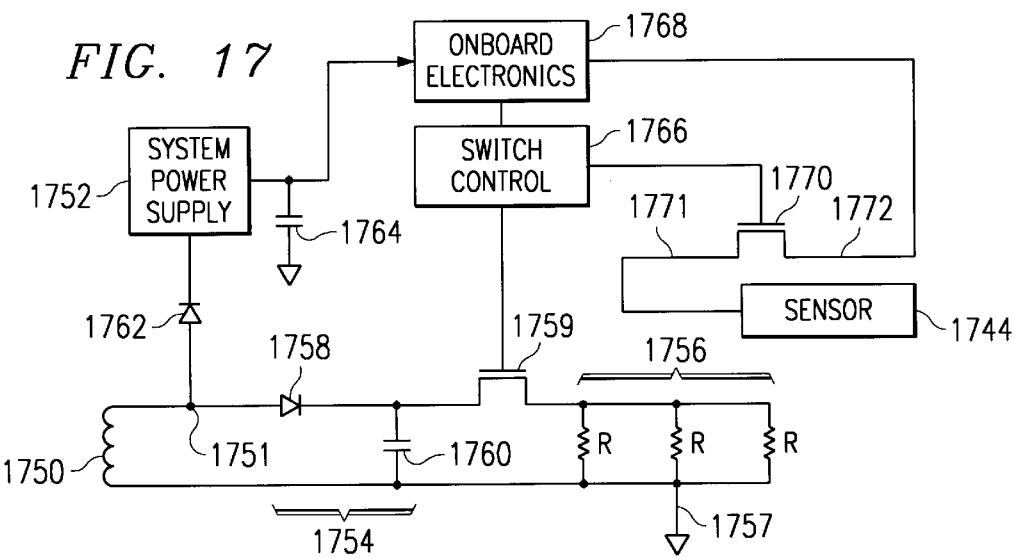
FIG. 17 illustrates a general circuit block diagram of the power supply structure for both the onboard circuits and the heater section.

Referring now to FIG. 17, there is illustrated a general circuit block diagram of the power supply structure for both the onboard circuits and a portion of the heater section. It can be appreciated that independent power supplies are suggested, since implementation of a single power supply source for both the heaters and the onboard system electronics may cause a momentary voltage variation (or power spike) in the system power such that operation of the control electronics could be disrupted. Therefore, an onboard coupling element 1750 (e.g., an inductor) is provided to power two power sources; a system power supply 1752 for all onboard electronics, and a heater power supply 1754 for a heater section 1756. The control system 1100 radiates energy through the radiating antenna 1104 which is coupled into the coupling element 1750.

Power for a portion of the heater section 1756 passes through a blocking diode 1758 and is stored in a capacitor 1760. The anode of the diode 1758 connects to a node 1751. The cathode connects to the upper plate of the capacitor 1760, and to one drain/source leg of a switching transistor 1759. The other drain/source leg of the switching transistor 1759 connects to the parallel resistances R of the heater section 1756. The lower plate of the capacitor 1760 connects to a ground potential node 1757, which can be the substrate of the semiconductor thermal-sensing ball 1101. The heater resistances R and the lower leg of the coupling element 1750 also connect to this ground node 1757. The gate of the heater switching transistor 1759 connects to a switching control circuit 1766 for operational control of the switching transistor 1759 for ultimately enabling current to flow from the coupling element 1750 and the heater capacitor 1760 to the heater section 1756. The voltage drop across the diode 1758 is minimal, but any losses can contribute to the overall heating effect for tumor ablation. Thus, a Schottky diode may be utilized for diode 1758 with a lower forward drop. The capacity for the heater capacitor 1760 may be realized by utilizing the lower hemisphere of the substantially spherical thermal-sensing ball 1176 or even a separate ball.

Similarly, power to the system electronics passes through a blocking diode 1762 to the system power supply 1752. The anode of the diode 1762 connects to the upper leg of the coupling element 1750, which is the node 1751. The cathode connects to the system power supply block 1752. At the output of the system power supply block 1752 is a power capacitor 1764 which stores charge for operation of the onboard system electronics, and also provides a smoothing function for any power fluctuations that may occur. The output of the system power supply 1752 connects to provide power to an onboard electronics block 1768, which represents the processor 1638, A/D converter 1646, RF I/O 1640, ID memory 1642, and other circuits not illustrated. The onboard electronics functions to control the switch control circuit 1766 according to stored instructions, or to instructions transmitted from the control system 1100 to the one or more thermal-sensing balls 1101. The onboard electronics 1768 also function to control a sensing transistor 1770 to read the output of the sensor 1744 via the gate of the sensing transistor 1770. One drain/source leg 1771 of the sensing transistor 1770 connects to the sensor 1744, while the other drain/source leg 1772 connects back to the onboard electronics 1768.

Figure 18:
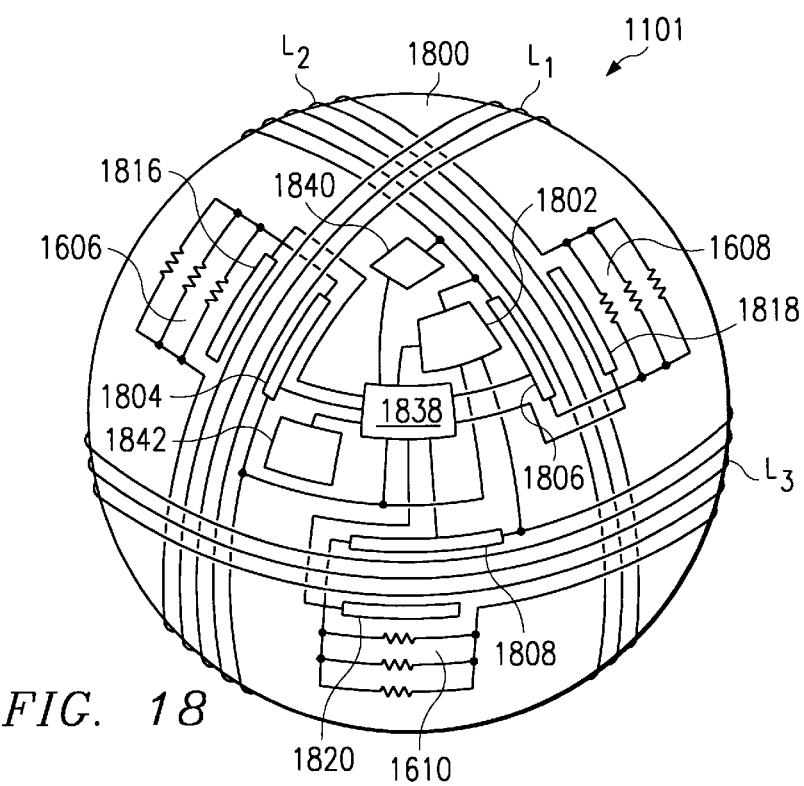
FIG. 18 illustrates a physical diagram of a thermal-sensing ball and associated exposed circuit blocks.

Referring now to FIG. 18, there is illustrated a physical diagram of a thermal-sensing ball 1101 and associated exposed circuit blocks. The ball 1101 comprises a substrate 1800 upon which the numerous onboard circuit elements are fabricated. The coils $L_1$, $L_2$, and $L_3$ are oriented substantially orthogonally to one another for coupling energy and signals to the circuits of the ball 1101 when in any orientation within the body, and transmitting signals therefrom. One end of each of the coils L, $L_2$, and $L_3$ is connected to a power regulator 1802, and respective control switches 1804, 1806, and 1808 (similar to control switches 1230, and 1766), which control switches are controlled by the microprocessor 1838. The other end of each of the three coils $L_1$, $L_2$, and L3 is connected to respective resistive ladders of heating element sections 1606, 1608, and 1610 (similar to resistive elements R of heater section 1756). The microprocessor 1838 provides monitor and control functions for all activities on the thermal-sensing ball 1101. The microprocessor 1838 is illustrated as comprising the A/D function of the A/D 1236, which combined functions can be found in conventional digital signal processing (DSP) circuits. The microprocessor 1838 connects to and controls the three switches 1804, 1806, and 1808 for controlling the amount of energy coupled from each of the respective coils $L_1$, $L_2$ and $L_3$ to respective heating elements 1606, 1608, and 1610. It can be appreciated that the microprocessor 1838 can be programmed from the control system 1100 to cycle power to each of the heating elements 1606, 1608, and 1610 in a predetermined fashion. For example, energy switched in the form of current to heating element 1606 may be cycled once every time period, while current switched to heating element 1608 is switched ten times per the same time period, and current switched to heating element 1610 is switched twenty-five times per the same time period. This flexibility offers more accurate and effective control of heat being applied by the thermal-sensing balls 1101 to the desired tissues or perhaps the drugs to be delivered.

The power regulation circuit 1802 connects to each of the unswitched sides of the coils $L_1$, $L_2$ and $L_3$ to obtain the maximum power transmitted. For example, if the orientation of the ball 1101 is such that the coupled power signal is the greatest on coil $L_3$, yet weaker on coils $L_1$ and $L_2$, the maximum power is still obtainable. Had the power regulator been connected to only a single coil, the amount of power coupled to the ball 1101 would be problematic based upon the orientation of the coils in the electric field provided by the control system 1100. As mentioned hereinabove, the power regulator 1802 provides power to all onboard circuits during operation of the ball 1101.

In close proximity to each set of heating elements 1606, 1608, and 1610, respective temperature sensors 1816, 1818, and 1820 are fabricated to accurately monitor the temperature of the respective heating elements. In this way, all or selected ones of the heating elements 1606, 1608, and 1610 can be monitored to obtain more accurate control of the desired heating effect. Each temperature sensor 1816, 1818, and 1820 connects to the microprocessor 1838 for power, AID conversion, and processing of the measured data.

The RF transmit/receive circuit 1840 connects to the microprocessor to provide I/O functions for RF signals coming into the ball 1101 from the control system 1100, and for the transmission of communication signals from the ball 1101 to the control system 1100. The RF circuit 1840 is illustrated as having a single connection to coil/antenna $L_2$, when in practice it could be connected to any or all three coils $L_1$, $L_2$ and $L_3$ to ensure adequate reception and signal transmission strength to the control system 1100. The RF transmit/receive circuit 1840 can also obtain power through the connection from the microprocessor 1838, or have its own dedicated connection (not shown) from the power regulator circuit 1802. Note that the coils $L_1$, $L_2$ and $L_3$ are used for power coupling and signal communication between the ball 1101 and the control system 1100. Therefore, the communication signal may be modulated into the power signal to provide a more continuous exchange of power and signals. Additionally, the number of coil windings can be varied according to the required power levels.

A memory 1842 (similar to memories 1120 and 1642) connects to the microprocessor 1838, is non-volatile, and stores the unique ID of the ball 1101. The unique ID can be accessed upon command from the control system 1100. It can be appreciated that the memory 1842 can be programmed according to the user's needs. For example, in addition to the unique ID, the memory 1842 may contain information related to the patient, such as name, address, date of usage of the ball 1101, the attending physician and hospital, circumstances under which the ball was used (e.g., drug delivery), etc. Additionally, where an aggregate (500, 700, or 1000) of balls 1101 are used, a subgroup of the balls 1101 may be programmed with a common ID such that during operation, that subgroup of balls 1101 may be energized, while others are not. This feature may be used where more than one aggregate (500 or 700) is implanted in the body, each aggregate (500, 700, or 1000) delivering drugs under different conditions at different sites. Notably, the unique ID can be programmed at the site by the control system 1100 prior to introduction of the ball aggregate (500, 700, or 1000) into the body, or after implantation.

Figure 19:
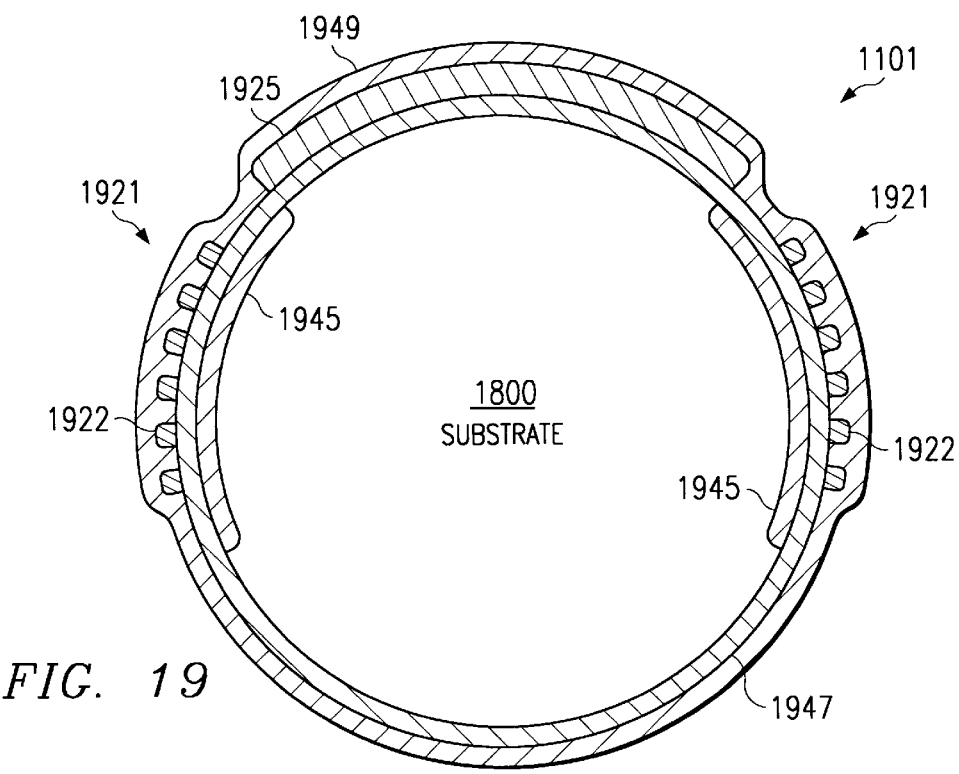
FIG. 19 illustrates a general cross section of a thermal-sensing ball.

Referring now to FIG. 19, there is illustrated a cross section of a thermal-sensing ball. The ball 1101 preferably comprises a spherical-shaped semiconductor substrate 1800 on which an integrated circuit has been formed, and which may be doped with P-type or N-type impurities in accordance with the particular requirements of the fabrication process. Semiconductor circuitry, indicated generally at 1945, resides on substrate 1800, and includes the power regulator 1840, an RF interface circuitry 1802 with mixing circuit and amplifier, as well as other circuitry. Substrate 1800 and circuitry 1945 are covered by an insulating layer 1947. Insulating layer 1947 is preferably formed of silicon dioxide or phosphosilicate glass. A temperature sensor 1925 is disposed on the surface of insulating layer 1947. Suitable connections are provided through the insulating layer 1947 to circuitry 1945.

A power and transmit/receive coil 1921 (only one shown, and similar to each coils $L_1$, $L_2$ and $L_3$, power coil 128, and antenna/coil 1104) is formed of helically-wrapped windings over the insulating layer 1947. The power coil 1921 may have any number of individual windings 1922 which can be fabricated from a deposited layer of aluminum that is patterned and etched using conventional semiconductor fabrication techniques. The actual number of individual windings of power coil 1921 may be far greater than the six illustrated.

The ball 1101 is coated with or encapsulated in a layer 1949 of biologically inert material such as phosphosilicate glass. The coating 1949 can withstand the acidity of the stomach to a pH level of about 1.5, and it is not subject to the enzymatic actions in the digestive tract, or other body chemicals to which it is subjected. The ball 1101 is substantially spherical and preferably about one millimeter in diameter. The very small size and round shape facilitates use with a catheter system, and for implantation. However, the ball 1101 should be made large enough to prevent absorption through structures in which the balls 1101 are to be implanted, for example, if the balls 1101 are to be used in the digestive tract, the microvilli in the lining of the digestive tract.

Figure 20:
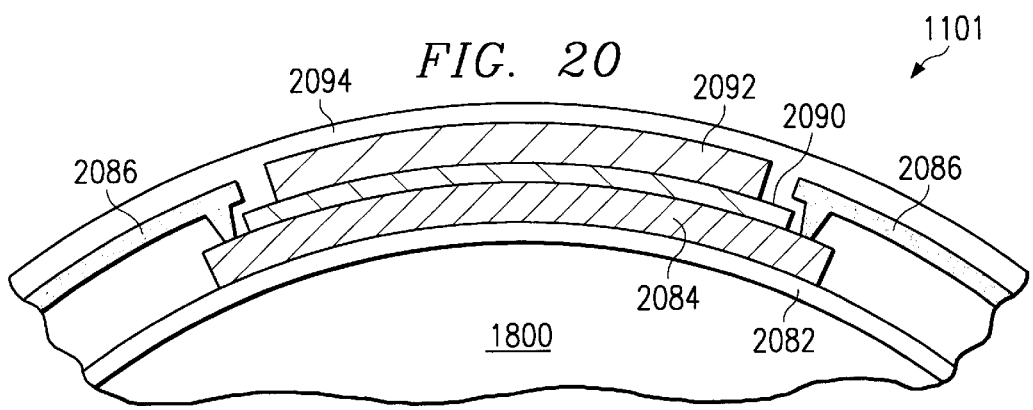
FIG. 20 illustrates an example of a semiconductor heating device as fabricated on the surface of a ball, according to a disclosed embodiment.

Referring now to FIG. 20, there is illustrated a semiconductor heating device, according to a disclosed embodiment. The thermal-sensing ball 1101 has associated therewith one or more sets of heating elements 1606, 1608, and 1610 which are formed onto the substrate 1800. A passivation layer 2082 is formed over the substrate 1800, and consists of $SiO_2$. Overlying the passivation layer 2082 is a poly layer 2084 of approximately 600 angstroms. The polycrystalline layer 2084 is appropriately doped to provide the resistive properties for the desired thermal output. A metal layer is then deposited and etched to form metal contacts 2086 at both ends of the poly layer 2084. Current is conducted through the metal contacts 2086 through the poly layer to provide the thermal effect. Another passivation layer 2090 is formed over the poly/metal layers (2084 and 2086, respectively) to provide isolation from the underlying poly layer 2084 and an overlying metal heat sink 2092 then disposed on he surface of layer 2090. The metal heat sink 2092 can be made of an aluminum and copper alloy for ready thermal sinking of the underlying heat generated by the resistive poly layer 2084. Finally, an overlying passivation layer 2094 is provided to electrical isolate all circuitry on the thermal-sensing ball 1101 from the contact medium.

Notably, it may be desirable to fabricate the heating elements 1606, 1608, and 1610 on the surface of the ball 1101 which is away from the onboard electronics (except the temperature sensor which measures the output of the thermal circuits) to provide a level of electrical stability to such circuits during the heating phase. This approach may be more conducive to a situation where the heating and temperature-sensing components are fabricated on a first ball, and the control electronics are fabricated on second ball which interfaces to the first ball. In this case, a third ball may be fabricated to provide an independent and stand-alone power source, independent from the transmitted power of the control system 1100. This will be discussed in greater detail hereinbelow.

As an alternative to providing both heating and temperature sensing on each thermal-sensing ball 1101, the heating and sensing functions can be separated such that distinct temperature sensing-only balls can be connected to the aggregate (500, 700, or 1000) along with a larger number of thermal-only balls. For example, ten temperature sensing-only balls can be interconnected with fifty thermal-only balls, all of which are implemented into the aggregation (500, 700, or 1000) to more effectively produce the desired results and measure the desired parameters. This technique permits a more direct resultant measurement of the effectiveness of the heating operation.

In alternative embodiments, the sensing portion of the balls 1101 can also be fabricated to include sensors that detect pH, $O_2$, and $CO_2$ content to help the physician determine when all the drug has had the desired effect, since unhealthy or affected tissue will have a different pH, $O_2$, and $CO_2$ content than normal healthy tissue. Additionally, the thermal balls 1101 can also be used to ablate other non-cancerous tissues or organs such as abnormally enlarged spleen, uterine fibroid, and endometriosis. The disclosed architecture can also be used for various vascular tumors such as hemangiomas, spider talecgentasia, and arterial venousmal formations, to name a few.

Figures 21A, 21B, 21C:
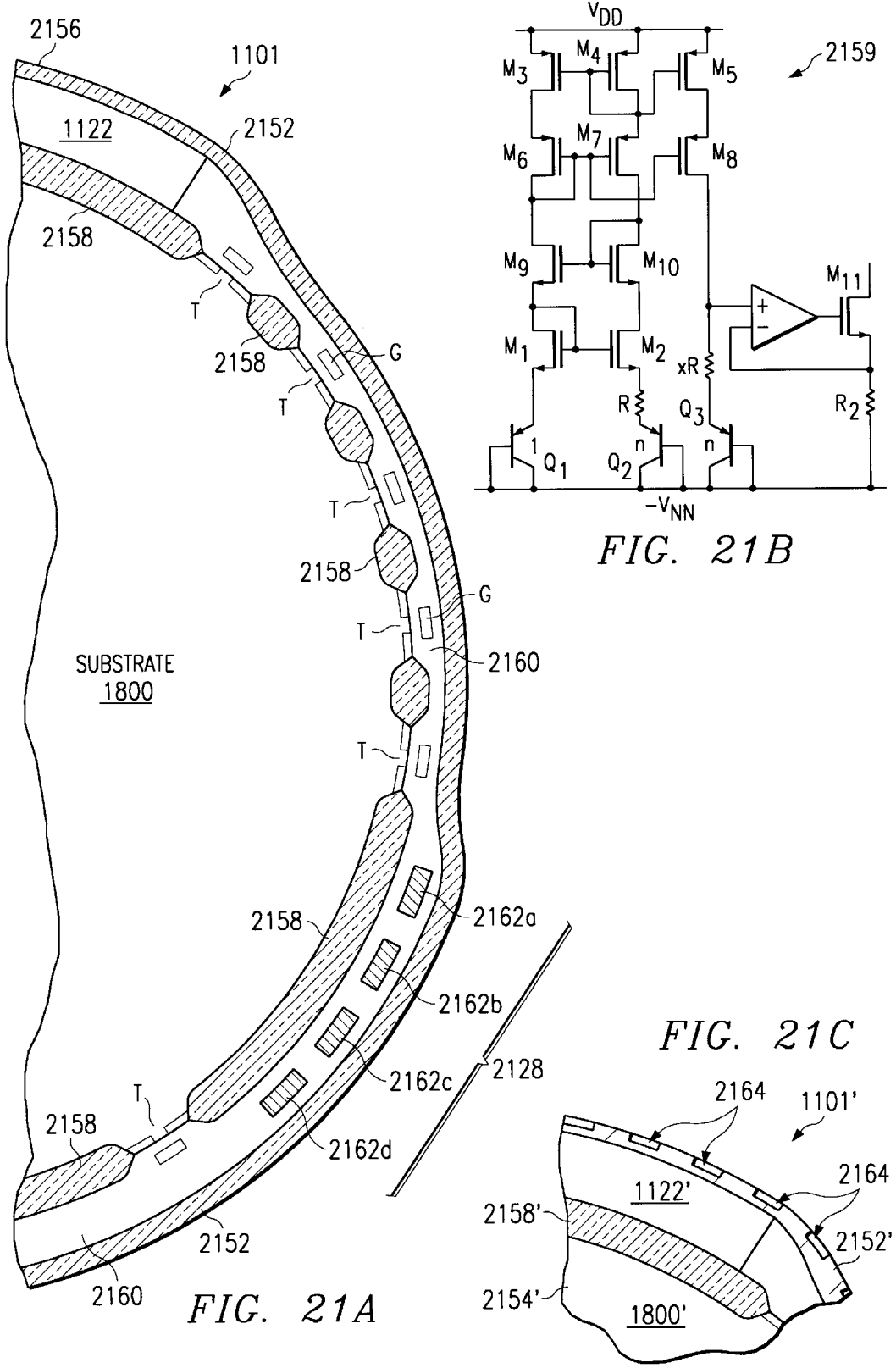
FIG. 21A illustrates a more detailed semiconductor structure of a thermal-sensing ball.
FIG. 21B illustrates a schematic diagram of a temperature-compensated current source used as a sensor for monitoring temperature.
FIG. 21C illustrates a portion of the ball having recessed areas for inhibiting tissue adhesion.

Referring now to FIG. 21A, there is illustrated a more detailed semiconductor cross section of the ball 1101. The ball 1101 is hermetically protected by a thin exterior glass passivation layer 2152, which may be phosphosilicate glass (PSG). The interior of the ball 1101 comprises the semiconductor substrate 1800, which may be doped p-type or n-type in accordance with the particular requirements of the fabrication process. Optionally, the substrate 1800 may be connected to a stent or other metallic intraluminal device to serve as a ground potential for the ball 1101. The temperature transducer 1122 (similar to 126 and 1744) has an outer surface 2156 that is exposed to the drug or surrounding tissue when implanted in the body. The transducer 1122 (and similarly for transducers 126 and 1744) preferably is formed atop a thick dielectric layer 2158, which may be a field oxide layer grown on the substrate 1800. Note that a lesser or greater number of transducers and coils may be used to achieve the desired results.

A large number of transistors T make up the circuitry of the voltage regulator 1840, microprocessor 1838, and other onboard circuits described hereinabove. Although these transistors T are schematically depicted as MOS transistors, the integrated circuitry of the ball 1101 could also use bipolar transistors. The individual transistors T are shown separated by portions of the field oxide 2158. Transistor gates G and circuit interconnections (not shown) are embedded in an inter-level dielectric layer 2160, and are made using conventional semiconductor fabrication techniques adapted to the spherical surface of the ball 1101.

The antenna/power coil 2128, described in connection with FIG. 19 as item 1921, is shown as having a plurality of separate windings 2162a, 2162b, 2162c and 2162d, which may be fabricated from a deposited layer of aluminum (or copper) that is patterned and etched using conventional semiconductor fabrication techniques adapted to the spherical shape of the ball 1101. The windings (2162a, 2162b, 2162c, and 2162d) are insulated from each other by portions of the inter4evel dielectric layer 2160. The actual number of individual windings of the coil 2128 may be far greater than the four specific windings shown. The ends of the coil 2128 are connected by additional conductors (not shown) to other circuit elements of the ball 1101.

Referring now to FIG. 21B, there is illustrated a schematic diagram of a temperature-compensated current source 2159. The current source 2159 is comprised of two legs. The first leg has disposed between a positive and negative rail, four MOS transistors and a bipolar transistor. The first MOS transistor is a P-channel transistor labeled $M_3$ having a source/drain path connected between a positive rail and the source-drain path of a P-channel transistor $M_6$. The other side of the source/drain path of transistor $M_6$ is connected to the gate thereof, and also to the one side of the source/drain path of N-channel transistor Mg, the other side thereof connected to one side of the source/drain path of an N-channel transistor $M_1$, and also to the gate of transistor $M_1$. The other side of the source/drain path of transistor $M_1$ is connected to the emitter of a P-channel transistor $Q_1$. The base and collector of transistor $Q_1$ are connected to the ground terminal. The other leg of the current source has a P-channel transistor $M_4$ with one side of the source/drain path thereof connected to the positive rail, the other side thereof connected to one side of the source/drain path of a P-drain transistor $M_7$ and also to the gate of transistor $M_4$ and the gate of transistor $M_3$.

The other side of the source/drain path of transistor $M_7$ is connected to one side of the source/drain of N-channel transistor $M_{10}$ and also to the gate of transistor $M_7$ and the gate of transistor $M_6$, and also to the gate of transistor $M_{10}$. The other side of the source/drain path of transistor $M_{10}$ is connected to one side of the source/drain path of an N-channel transistor $M_2$, the gate thereof connected to the gate of transistor $M_1$ (the gate of transistor $M_{10}$ connected to the gate of transistor $M_9$ and the gate of transistor $M_7$ connected to the gate of transistor $M_6$). The gate of transistor $M_2$ is connected to the gate of transistor $M_1$. The other side of the source/drain path thereof is connected to one side of a resistor R. The other side of resistor R is connected to the emitter of a PNP transistor $Q_2$, the base and collector thereof connected to ground. The transistors $M_1$–$M_4$, $M_7$ and the bipolar transistors $Q_1$ and $Q_2$, form a conventional supply-independent circuit. The leg associated with transistor $Q_1$ provides the reference link with the current source, and the transistor's associated leg in bipolar transistor $Q_2$ provide the function of the mirror leg.

The current through transistor $M_4$ is utilized to generate a bias voltage on the gate of transistor $M_3$ to control a current therethrough. Therefore, the current through transistor $M_4$ is essentially reflected over to transistor $M_3$ such that the current through transistor $M_3$ is equal to the current through transistor $M_4$. The transistors $M_1$ and $M_2$ allow a voltage on the emitter of transistor $Q_1$ to be reflected over to the top of resistor R such that the voltage on the emitter of transistor $Q_1$ and the voltage on the top of resistor R are substantially equal. The current through resistor R generates a voltage $\Delta V_{BE}$ thereacross, which represents the difference in the base-emitter voltages of the two transistors $Q_1$ and $Q_2$. Although the current is equal through both base-emitter junctions of transistors $Q_1$ and $Q_2$, there is a small difference in the base-emitter voltage, this being the voltage developed across the resistor R, this being a Temperature Proportional to Absolute Temperature (TPAT). This current is subtracted from a temperature-stable current to therefore provide an offset current. This offset current is inversely proportional to temperature.

The gates of transistors $M_3$ and $M_6$ are output to two series-connected P-channel transistors $M_8$ and $M_5$, respectively, disposed between the positive supply and the positive input of a unit gain amplifier. This positive input is also connected to one side of a bias resistor, the other side of which is connected to the emitter of a PNP transistor $Q_3$, the base and collector thereof connected to ground. The output of the amplifier is connected to the gate of N-channel transistor $M_{11}$, the drain thereof connected to the negative input of the amplifier, and also to one side of an output load resistor $R_2$, connected on the other side thereof to ground. The source of transistor $M_{11}$ provides a voltage output, which constitutes a temperature-dependent voltage.

Referring now to FIG. 21C, there is illustrated a portion 1101' of the ball 1101 having recessed portions, using similar reference numerals which designate similar elements. The recessed portion 1101' includes a substrate 1800' on which a thick field oxide 2158' has been grown. Overlying the thick field oxide 2158' is a transducer area 1122' whose outer surface has been modified with recessed areas 2164. The recessed portion 1101' of dielectric layer 2152' overlying the transducer area 1122' has recesses 2164 formed in its outer surface. These recesses 2164 may also extend beyond the edges of the transducer area 1122' at least so far as the surface of the ball 1101' may be exposed to the desired medium.

The purpose of the recesses 2164 is to inhibit tissue adhesion to the surfaces of the ball 1101' that are exposed to the medium to be measured. Tissue adhesion is known to occur on the surfaces of implants through the attachment of fibroblasts. This phenomenon is well known and is described in Von Recum et al., "Surface Roughness, Porosity, and Texture as Modifiers of Cellular Adhesion," Tissue Engineering, Vol. 2, No. 4, 1996 (available from the Dept. of Bioengineering, Clemson University, Clemson, S.C.). The recesses 2164 are presently preferred to be about one micron deep, three microns wide, and spaced three microns apart in a checkerboard topography. Such recesses can be fabricated by conventional selective etching techniques adapted to the spherical shape of the ball 1101.

Figure 22:
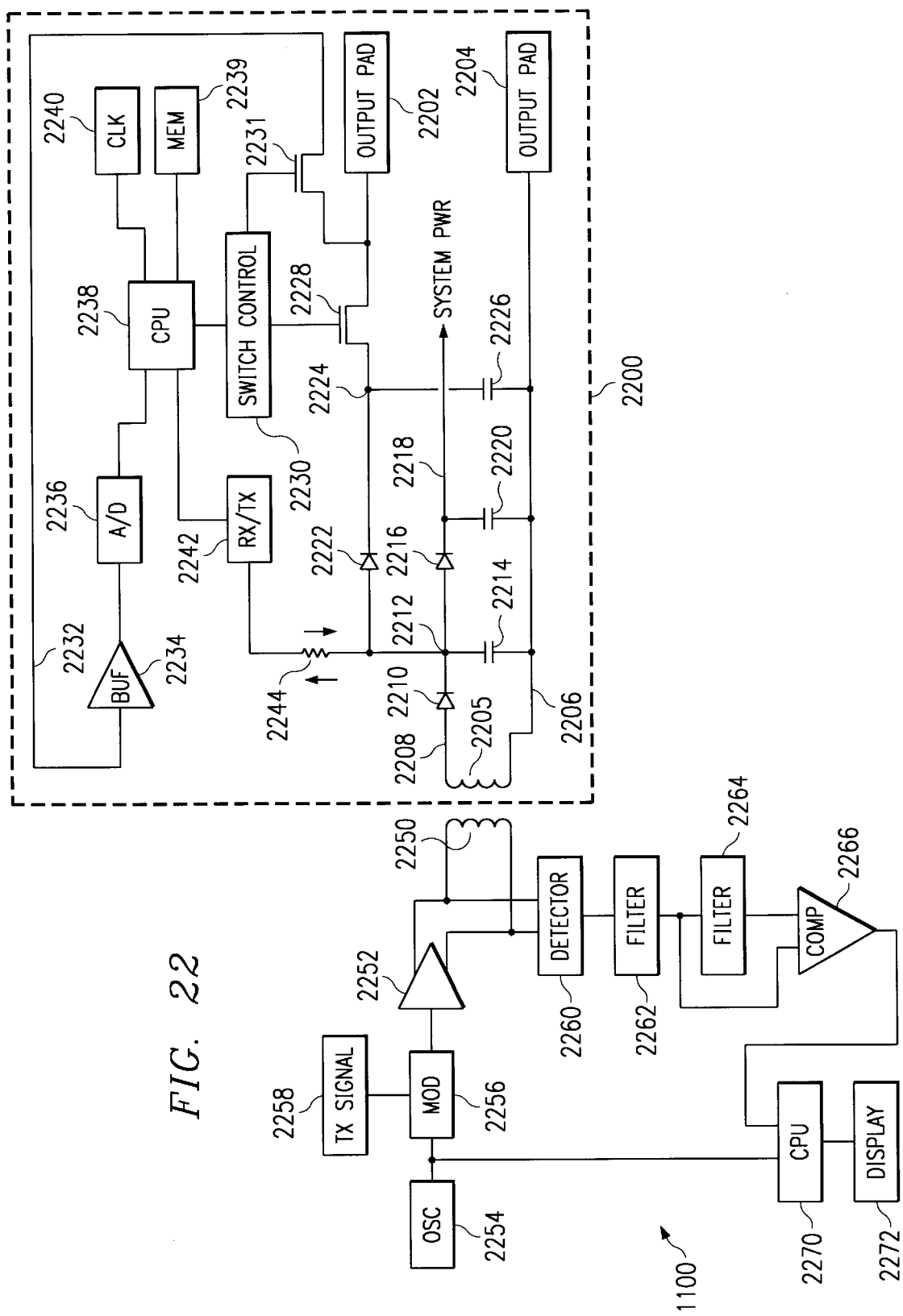
FIG. 22 illustrates a schematic block diagram of an alternative embodiment having a stimulus (or actuator) function and the external control system for the powering/detection operation, which may be used in conjunction with a drug infusion system.

Referring now to FIG. 22, there is illustrated a schematic block diagram of an alternative embodiment having a stimulus (or actuator) function and the external control system for the powering/detection operation. The actuator circuit 2200 is operable to provide two output interfaces, the output pad 2202 as an anode and the output pad 2204 as a cathode, for interfacing with the medium to be stimulated. The spacing between these two pads or contacts 2202 and 2204 is approximately 0.5 cm. The illustrated embodiment is that associated with a "passive" system, which term refers to the fact that there is no battery associated therewith. In order to operate the system, there is provided the inductive coupling element 2205 in the form of an inductor, which is operable to pick up an alternating wave or impulse via inductive coupling and extract the energy therein for storage in the inductive element 2205. This will create a voltage across the inductive element 2205 between a terminal 2206 and a terminal 2208. A diode 2210 is connected between the node 2208 and a node 2212, with the anode of diode 2210 connected to node 2208 and the cathode of diode 2210 connected to a node 2212. Typically, the diode 2210 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 2210 is operable to rectify the voltage across the inductive element 2205 onto the node 2212, which has a capacitor 2214 disposed between node 2212 and node 2206. Node 2212 is also connected through a diode 2216 having the anode thereof connected to node 2212 and the cathode thereof connected to a node 2218 to charge up a capacitor 2220 disposed between node 2218 and 2206. The capacitor 2220 is the power supply capacitor for providing power to the actuator circuit 2200. The capacitor 2214, as will be described hereinbelow, is operable to be discharged during operation of the system and, therefore, a separate capacitor, the capacitor 2220, is required for storing power to power the system.

The node 2212 is connected to the anode of a diode 2222, the cathode thereof connected to a node 2224. A main capacitor 2226 has one side connected to node 2224 and the other side thereof connected to node 2206. The capacitor 2226, as will be described hereinbelow, is operable to provide the primary discharge energy to, for example, any medium desired via the output pad 2202, the anode of the actuator circuit 2200. This node 2224 is connected to one side of the gate/source path of a drive transistor 2228, the other side thereof connected to the output pad 2202. The gate of drive transistor 2228 is connected to the output of a switch control circuit 2230. Drive transistor 2228 is operable to be turned on for a short period of time to connect to the top plate of capacitor 2226 to the output pad 2202, and subsequently, to conduct current to the desired tissue or point.

In addition to transmitting energy out on output pad 2202, there is also provided a sense transistor 2231 which has one side of the gate/source path thereof connected to the output pad 2202 and the other side thereof connected to a node 2232. The gate of sense transistor 2231 is connected to the output of the switch control 2230. Node 2232 is connected to the input of a buffer 2234 to generate an analog signal output thereof which is then converted with an analog-to-digital converter 2236 to a digital value for input to a CPU 2238 (similar to CPU 1238). The CPU 2238 is operable to receive and process this digital input voltage. A clock circuit 2240 is provided for providing timing to the system. A memory 2239 is provided in communication with the CPU 2238 to allow the CPU 2238 to store data therein for later transmittal back to the control system 1100 or for even storing received instructions. This memory 2239 can be volatile or it can be non-volatile, such as a ROM. For the volatile configuration, of course, this will lose all information when the power is removed.

The CPU 2238 is operable to provide control signals to the switch control 2230 for turning on the drive transistor 2228 or the sense transistor 2231 at the appropriate time. Typically, the drive transistor 2228 is controlled to turn on for a period of approximately 0.5 microseconds 60–80 times per minute. Once drive transistor 2228 is turned off, then sense transistor 2231 can be turned on. Alternatively, sense transistor 2231 could be a pass-through circuit such that the CPU 2238 can always monitor the voltage on the output pad 2202. However, it is desirable with the sense transistor 2231 and the sensing operation to sense depolarization in the desired tissue after an output voltage has been provided thereto for a short duration of time.

In order to communicate with the CPU 2238 for transferring data thereto and for allowing the CPU 2238 to transfer data therefrom, the receive/transmit circuit 2242 is provided for interfacing to node 2212 to a resistive element 2244. This allows RF energy to be transmitted to node 2212. It is important to note that the semiconductor junction across diode 2210 is a capacitive junction. Therefore, this will allow coupling from node 2212 to node 2208. Although not illustrated, this could actually be a tuned circuit, by selecting the value of the capacitance inherent in the design of the diode 2210. In any event, this allows an RF connection to be provided across diode 2210 while allowing sufficient energy to be input across conductive element 2205 to provide a voltage thereacross for rectification by the diode 2210 and capacitor 2214. Typically, the operating frequency of this connection will be in the MHz range, depending upon the design of which a variety are possible. For example, some possible designs are illustrated in U.S. Pat. No. 4,333,072 entitled "Identification Device," issued Jun. 1, 1982, and Mogi et al., U.S. Pat. No. 3,944,982, entitled "Remote Control System For Electric Apparatus," issued Mar. 16, 1976. With these types of systems, power can continually be provided to the node 2212 and subsequently to capacitors 2220 and 2226 to allow power to be constantly applied to the actuator circuit 2213. The diode 2222 may not be required in order to provide the sufficient charge to capacitor 2226, but some type of isolation is required between the capacitor 2226 and the capacitor 2220. Voltage regulation may also be required in order to provide a shaped pulse on the output pad 2202. This could be provided by the switch control 2230.

The control system 1100 may be disposed external to the body and proximate to the actuator circuit 2200, or internal to the body, and remotely located or proximate thereto, includes an inductive element 2250 which is operable to be disposed in an area proximate to the skin exterior to the body in the proximity of the actuator circuit 2200. The inductive element 2250 is driven by a driving circuit 2252 which provides a differential output that is driven by an oscillator 2254. This will be at a predetermined frequency and power level necessary to couple energy from inductive element 2250 to inductive element 2205. Since this is an external system, the power of the oscillator 2254 can be set to a level to account for any losses through the body tissues. To allow information to be transmitted, a modulation circuit 2256 is provided which is modulated by a transmitter signal in a block 2258 that allows information to be modulated onto the oscillator signal 2254, which oscillator 2254 provides a "carrier" signal. However, it should be understood that the information that is transmitted to the actuator circuit 2213 could merely be date information whereas the CPU 2238 could operate independent of the information being transmitted to provide the correct timing and wave shape for the output pulses. Alternatively, the entire control of the system may be provided by the transmit signal 2250 and the information carried thereon, because power must be delivered to the illustrated embodiment when there is a lack of an independent power source in the actuator circuit 2200.

The information received from the actuator circuit 2200 is modulated upon the oscillator signal driving the inductive element 2250. This information is extracted therefrom via a detector 2260 which has the output thereof input to a first low pass filter 2262 and then to a second low pass filter 2264. The output of low pass filters 2262 and 2264 are compared with a comparator 2266 to provide the data. The filter 2262 will provide an average voltage output, whereas the filter 2264 will provide the actual digital voltage output. The output of the comparator 2266 is then input to a CPU 2270 which also is powered by the oscillator 2254 to process the data received therefrom. This can be input to a display 2272.

Figure 23:
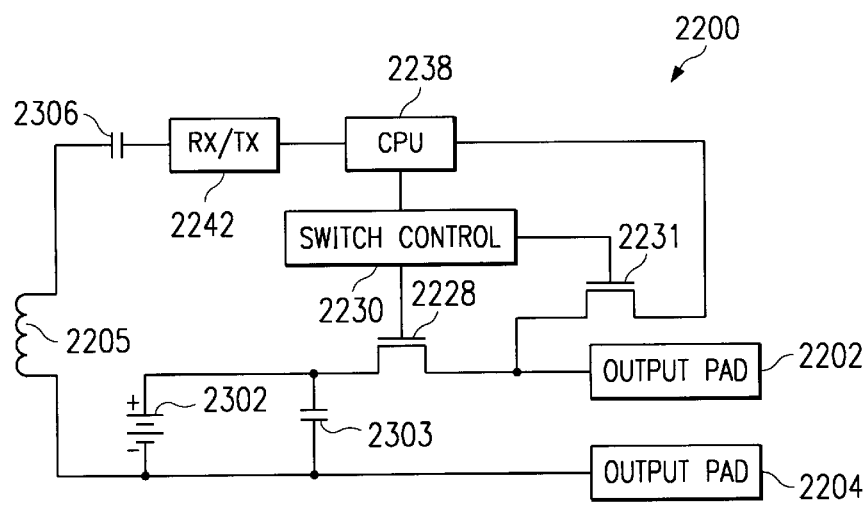
FIG. 23 illustrates a general block diagram of a stimulus circuit using a battery as a power source, and in conjunction with the disclosed drug infusion system.

Referring now to FIG. 23, there is illustrated a general block diagram of the stimulus circuit using a battery as a power source. The ball stimulus circuit 2200 comprises a battery 2302 which is connected to a capacitor 2303. The battery 2302 is provided across the capacitor 2303 to provide sufficient charge therefor. Additionally, the capacitance 2303 could actually be the capacitance of the battery 2302. Additional structure could be provided for powering the CPU 2238 and the other circuitry on the ball 2200 from the battery 2302. As such, there would only be required a smaller inductive element 2305 and a capacitor 2306 to allow the receive/transmit block 2242 to receive/transmit information from and to the remote control system 2200. The CPU 2238 controls the switch control circuit 2230, which in turn switches transistors 2228 and 2231 on or off. Turning transistor 2238 on, switches power to the stimulation output pad 2202, and drives the energy across the contacted medium to the return output pad 2204.

Figure 24A:
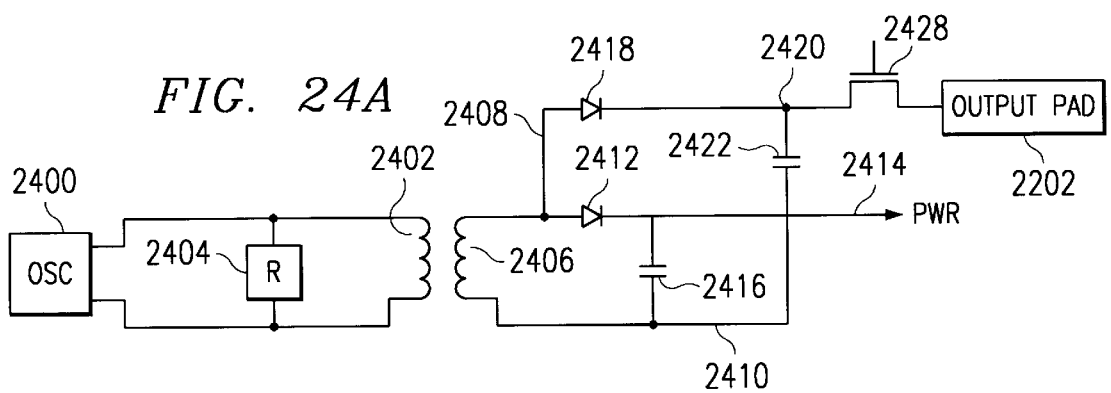
FIGS. 24A–C illustrate alternate embodiments for the transmit/receive operation of the stimulus embodiment.
Figure 24B:
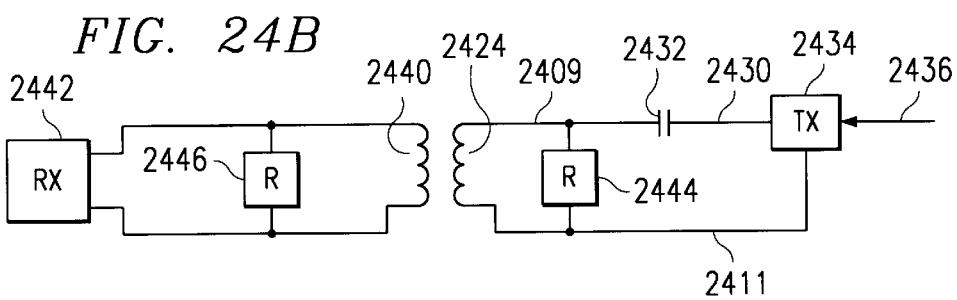
Figure 24C:
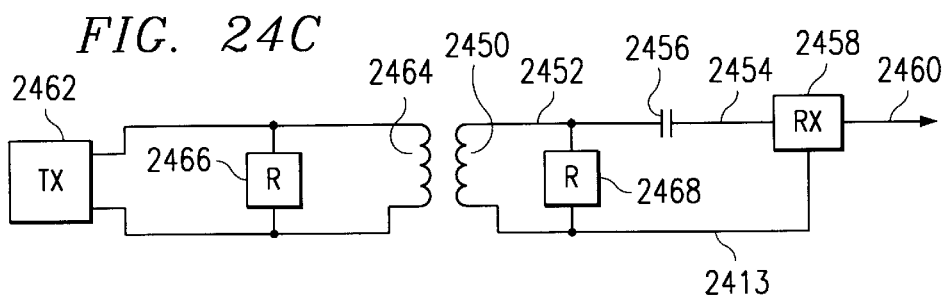

Referring now to FIGS. 24A–C, there are illustrated alternate embodiments for the transmit/receive operation of the actuator embodiment of FIG. 22. In FIG. 24A, there is provided an oscillator 2400 which drives an external inductive element 2402 which may be utilized to couple both electrical power and information or data. Typically, there is some type of load 2404 disposed across the inductive element 2402. A separate inductive element 2406 (similar to inductive element 2205), inductively coupled to inductive element 2402, is provided on the actuator ball 2200. Voltage generated across the inductive element 2406, connected between a node 2408 and a node 2410 is applied across rectifier 2412 connected between node 2408 and a power node 2414. A power supply capacitor 2416 disposed across node 2414 and node 2410 stores the rectified voltage for use by the circuit. Similarly, a rectifier 2418 is connected between the node 2408 and a node 2420 which is connected to one side of a main "surge" capacitor 2422. The other side of capacitor 2422 is connected to node 2410. This capacitor 2422 is similar to the main "surge" capacitor 2226 in FIG. 22. A switching transistor 2428 (similar to switching transistor 2228) is provided for connecting the node 2420 to the output pad 2202.

In the alternative embodiment of FIG. 24B, the receive operation utilizes a separate inductive element or antenna 2424 in the ball actuator 2200, which is operable to be connected between nodes 2409 and 2411. Node 2409 is capacitively coupled to a transmit node 2430 with a capacitor 2432, the capacitor 2432 being a coupling capacitor. A transmitter 2434 is provided for transmitting received data from a line 2436 to the node 2430, which is then coupled to the node 2409 to impress the RF signal across the inductive element 2424.

A corresponding inductive element 2440 is disposed on the external remote controller of control system 2200, which inductive element 2440 is operable to be disposed proximate to the inductive element 2424, either external to the human body, or internally where remotely or proximately located. The inductive element 2440 is basically a "pick-up" element which is operable to receive information and function as an antenna, and provide the received signal to a receiver 2442. The structure of FIG. 24B is a separate structure, such that node 2409 is isolated from node 2408, the power receiving node. However, it should be understood that any harmonics of the oscillator 2400 would, of course, leak over into the inductive element 2424. This can be tuned out with the use of some type of tuning element 2444 on the ball actuator 2200 disposed across inductive element 2424, and also a tuning element 2446 disposed across the inductive element 2440, i.e., the antenna.

Referring now to FIG. 24C, there is illustrated a simplified schematic diagram of the receive portion. The ball actuator 2200 has associated therewith a separate receive antenna or inductive element 2450 disposed between node 2413 and a node 2452. Node 2452 is capacitively coupled to a receive node 2454 with a coupling capacitor 2456. A receiver 2458 is provided for receiving the information transmitted thereto and providing on the output thereof data on a data line 2460. The receiver 2458 is operable to receive the RF signal, demodulate the data therefrom, and provide digital data on the output 2460. External to the human body and the ball actuator 2200 is a transmitter 2462 which is operable to impress a signal across an external inductive element 2464. The inductive element 2464 basically provides the RF energy and is essentially tuned with a tuning element 2466. A corresponding tuning element 2468 is provided on the ball actuator 2200 and disposed across inductive element 2450, the inductive element 2450 acting as an antenna, as well as the inductive element 2464.

Note that, in circumstances where the signals of the thermal-sensing ball 1101 cannot be adequately received therefrom and/or power coupled thereto, the antenna 1102 of the control system 1100 may need to be implanted proximate to the ball sensor 1101 in order to couple the transmit/receive signals and power. Furthermore, where more than one sensor ball 1101 is used, communication of power and data signals between the various ball sensors 1101 may need to employ distinct time periods (i.e., time multiplexing) when communication occurs using a single common frequency, or discrimination circuits may need to be used where communication occurs simultaneously with the plurality of implanted ball sensors 1101 having different oscillator frequencies.

Referring now to FIG. 25, there is illustrated a side view of an alternate embodiment having additional circuitry where the ball provides an actuator function to stimulate the tissues into which drugs are to be released. In one application, an actuator 2500 comprises two primary ball structures 2502 and 2504 which provide anode and cathode stimulation means, a power supply generating structure 2506 connecting the ball structures 2502 and 2504 for storing and providing a power supply voltage to the ball structures 2502 and 2504. Rectifying elements provided on the balls 2502 and 2504 (e.g., diodes, and not shown) must be provided for receiving and rectifying the power, and charging up a power supply capacitor, in addition to a main "surge" capacitor for providing a relatively large amount of pulsed energy, if such pulsed energy is desired for the particular application. The structure 2505 between the balls 2502 and 2504 may contain either a battery or a capacitor 2506 for providing stand-alone power for the assembly. This is disposed between interface supporting structure 2508 and 2510. The two primary balls 2502 and 2504 have respective output pad interfaces 2512 and 2514, respectively, for contacting the desired medium for stimulation.

Referring now to FIG. 26, there is illustrated a perspective view of a ball 1101 having a single transducer interface and the inductive element 1104 (inductive elements 1102 and 1922 being similar thereto) is illustrated as being strips of conductive material wrapped around the surface or near the surface of the ball 1101. The inductive element 1104 is formed of a conductive strip wrapped many times around the ball 1101. The length of inductive element 1104 depends upon the receive characteristics that are required. As described hereinabove with reference to FIGS. 24A–C, there could be multiple conductive strips, each associated with a receive function, a transmit function, or a power function, or they could all share one single conductive element or strip.

On one end of the ball 1101 there is provided a transducer interface 2600 of the transducer 1122 having, optionally, one or more interface balls 2602 (or partial balls, called nodules) associated therewith extending from the transducer interface surface to provide enhanced engagement of the measuring surface or physical entity and also utilized to more effectively transmit heat to the surrounding medium. The interface balls 2602 can be made of non-reactive material, e.g., gold to prevent degradation while in the body. Note that in some applications, the interface nodules 2602 are not required for obtaining the desired quantitative data, but can be used to transmit heat. On the other end of the ball 1101 are provided interconnect balls 2604 (or nodules) for interconnecting to one or more other substantially spherical balls which may provide similar functions such as monitoring of quantitative data, or unique functions such as supplying only power or data buffering and storage.

Referring now to FIG. 27, there is illustrated a cross-sectional view of an output pad of the actuator embodiment. In general, an output pad 2700 (similar to output pad 2202) is required to provide a conductive interface between the transistor 2228 and, for example, the medium which is to be stimulated. This therefore requires some type of metallic interface that is non-reactive. Such an interface would require a metal such as gold, platinum and the like. In the disclosed embodiment, gold would be provided.

After the formation of the upper metal layer via a deposition technique with metal such as aluminum or copper, a passivation layer of oxide 2702 is disposed over the substrate 2701 to basically prevent oxidation of the metal layers and protect the semiconductor circuits in general. The contact layer 2714 extends beyond the active region 2712 to an output pad region 2704 and is separated from the active region 2712 by a layer of field oxide 2710 or some type of isolation oxide. There may be some type of channel stop implant disposed below the field oxide layer 2710. The contact layer 2714 extends from the source/drain implant 2716 to the region 2704. This contact layer 2714 is required to be fairly conductive. Typically, polycrystalline silicon is not of sufficient conductivity to meet this requirement. Therefore, some type of polysilicide process will be required, wherein the upper surface is converted to some type of suicide such as titanium disilicide to lower the surface resistivity thereof. Alternatively, a metal layer could be provided which is connected to the contact region 2714.

Once the contact layer 2714 is formed and the passivation layer 2702 is disposed over the entire structure, vias 2706 are formed therein. These vias 2706 are then filled with metallic plugs 2708 by forming a layer of metal over the layer 2702 and then etching the layer 2702 to remove the undesired portions. The metal plugs 2708 may be formed of metal such as aluminum or gold. If they were formed of gold, this would allow for soldering if they were to be used as contacts. However, in this context, these plugs 2708 are utilized for conductivity purposes. Therefore, an aluminum plug would be sufficient if it were covered with a thin layer of gold to render the aluminum non-reactive and prevent oxidation thereof Alternatively, in the disclosed embodiment, the plug 2708 may, of course, be gold. However, it should be understood that any type of non-reactive metal could be utilized as long as the surface thereof is sufficiently non-reactive, and the conductance of the plug 2708 is sufficiently high to result in a low resistance path between the exterior of the spherical IC and a capacitive plate (not shown). The reason for this is that the stored charge must be discharged into a resistance as low as 500 Ohms and any significant resistance disposed between the upper plate of the capacitor and the exterior must be minimized.

Figure 28:
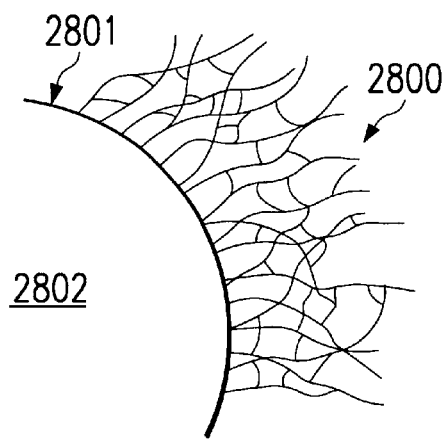
FIG. 28 illustrates a pH-sensitive hydrogel covalently attached to the surface of a ball semiconductor sensor according to a class of embodiments described in the present disclosure.

Referring now to FIG. 28, there is illustrated an embodiment having a hydrogel 2800 which is covalently attached to the surface 2801 of a semiconductor ball 2802 (similar in construction to ball 1101), but configured as a sensor. This hydrogel 2800 is pH sensitive, and undergoes very large changes in volume with small changes in local pH. This hydrogel 2800 changes volume manyfold over a small pH change. The hydrogel 2800 is covalently receptive to certain biologically active enzymes such as glucose oxidase. This enzyme catalyzes the reaction

$$\text{Glucose} + 2H_2O + O_2 \rightarrow \text{Gluconic Acid}^- + H_3O^+ + H_2O_2 \tag{1}$$

Therefore, the change in acid concentration (measurable as a pH change) is directly proportional to the glucose concentration. This allows the hydrogel 2800 then to serve as a very sensitive glucose sensor. With the appropriate degree of crosslinking, the gel 2800 can actually exert a contractile force on the semiconductor ball sensor 2802 on the order of $10^4$ dynes/cm. This contractile force is large enough to be measured as a pressure exerted on, for example, strain gauge sensors implanted on or near the surface of the semiconductor ball sensor 2802. This embodiment can therefore detect small changes in the local pH caused by the oxidation of glucose by the enzyme glucose oxidase. To prevent shifts in pH due to other reasons from giving a false reading, an aggregate of two semiconductor ball sensors 2802 will always be used clinically, where one of the semiconductor ball sensors 2802 contains the glucose oxidase enzyme and the other does not. Therefore, by examining the difference between the two ball sensors 2802, the effects due to the presence of glucose can be isolated.

Figure 29:
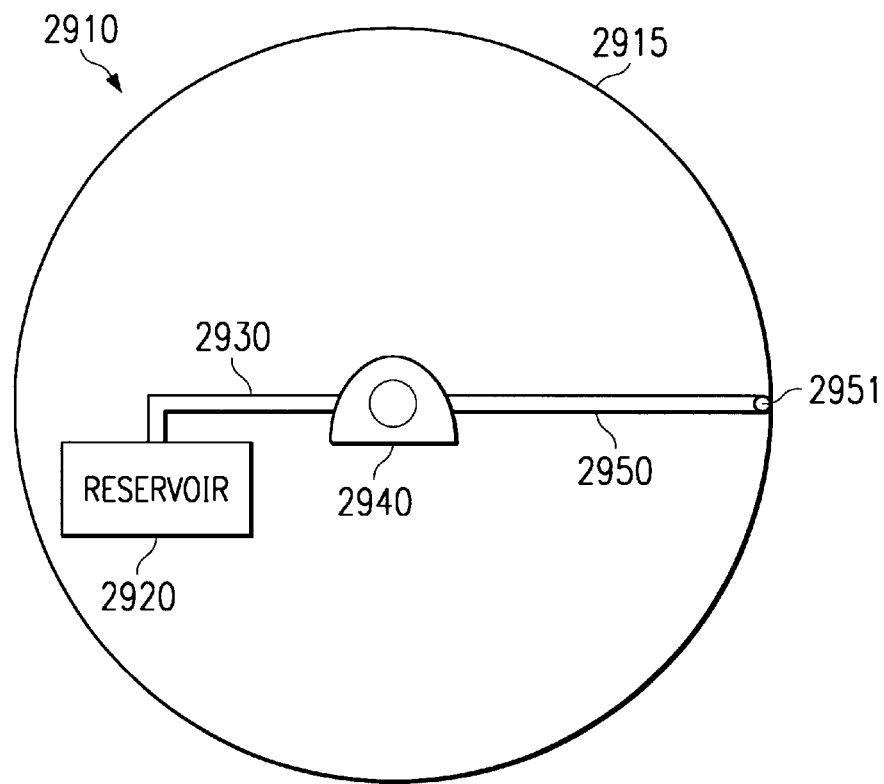
FIG. 29 illustrates a ball which is constructed with a pump that is connected on one end through plumbing to reservoir, and on a second end through plumbing to the surface of the ball.

Referring now to FIG. 29, there is illustrated one embodiment where a ball IC 2910 is constructed with a pump 2940 that is connected on one end through plumbing 2930 to reservoir 2920, and on a second end through plumbing 2950 to the surface 2915 of the ball IC 2910. A medicine carried by the ball IC 2910 in reservoir 2920 to a treatment site can be released to the site through plumbing 2930 and 2950. The action of pump 2940, controlled by the controller 1100 of FIG. 11, is responsive to signals generated by control logic 1118, also shown in FIG. 11. The disclosed architecture is provided as an implantable system for the delivery of medication locally to a site. However, it can also be engineered to deliver systemically acting substances such as insulin in response to certain levels of detected substances such as glucose. The ball 2910 can also accommodate one or more actuator devices which release pharmaceuticals and/or bio-pharmaceuticals for gene therapy.

In the brain, a site of electrical discharge (seizure focus) may be approached via blood vessel access for applying a local discharge of antiepileptiform medicine to provide for seizure control without systemic side effects. Similarly, chemotherapy, heat, or radiation can also be delivered locally to tumors via blood vessel access without far reaching effects. Further, robotic ICs may also deliver local laser or rotary ablative therapy to blood vessels located throughout the body including sites in the cerebral circulation currently inaccessible. Locally delivered ultrasound emitters may provide for better demonstration of blood vessels anatomy when used in combination with a conventional external ultrasound acoustic receiver.

As a further variation of the present system, a ball system is attached to a needle used for filling the drug reservoir. This ball system measures fluid flow using a light emitting diode and a light sensor. Additionally, the ball system can also have a sensor for determining hydrostatic pressure, for example, a strain gauge sensor. The ball system also has an RF coil to transmit data to a remote control system which may be external to the body, such as a computer for computation and analysis. By comparing the plot of flow versus pressure, the structural integrity of the reservoir can be confirmed.

Figure 30A:
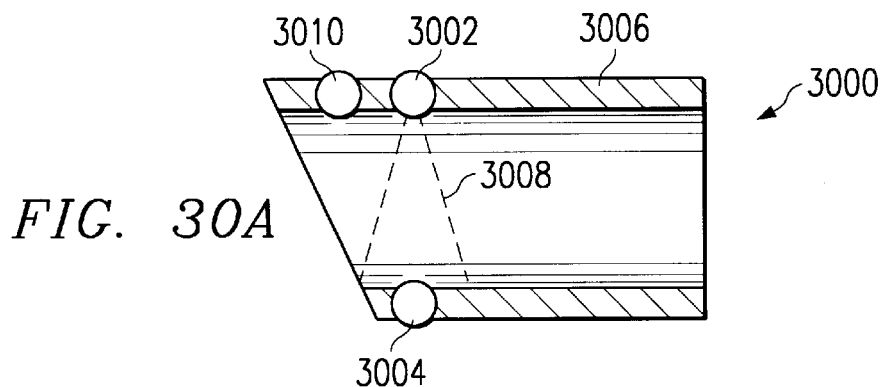
FIG. 30A illustrates a needle having a ball system integrated into or near its tip for measuring parameters during filling of the reservoir.

Referring now to FIG. 30A, there is illustrated a needle having a ball system integrated into or near its tip for measuring parameters during filling of the reservoir. A needle 3000 is sufficiently small for insertion into a reservoir, which may be or may not already be implanted in the body. An emitter ball 3002 sits substantially diametrically opposite a detector ball 3004, wherein each ball is implanted in the walls of the needle shaft 3006, and each having a portion of the surface of the respective balls exposed inwardly to the passing fluid (e.g., drug) such that some of the light rays 3008 emitted from an LED emitter circuit on the emitter ball 3002 impinge on a light detector circuit fabricated of the surface of the detector ball 3004, located in the wall of the needle shaft opposite the control ball 3002. Similarly, a pressure sensing ball 3010 may be implanted in a wall of the needle shaft 3006 having a sensing portion exposed to the fluid passing in the needle in order to measure fluid pressure. It can be appreciated that the functions of light detecting ball 3004 and the pressure sensing ball 3010 may be fabricated onto a single ball which has enough sensing surface area exposed to the fluid in order to make both measurements. Communications circuits may be fabricated on any or all of the balls to facilitate monitor and control of the balls with a remote (or external) control system employed for controlling, recording, and displaying data to an operator.

Figure 30B:
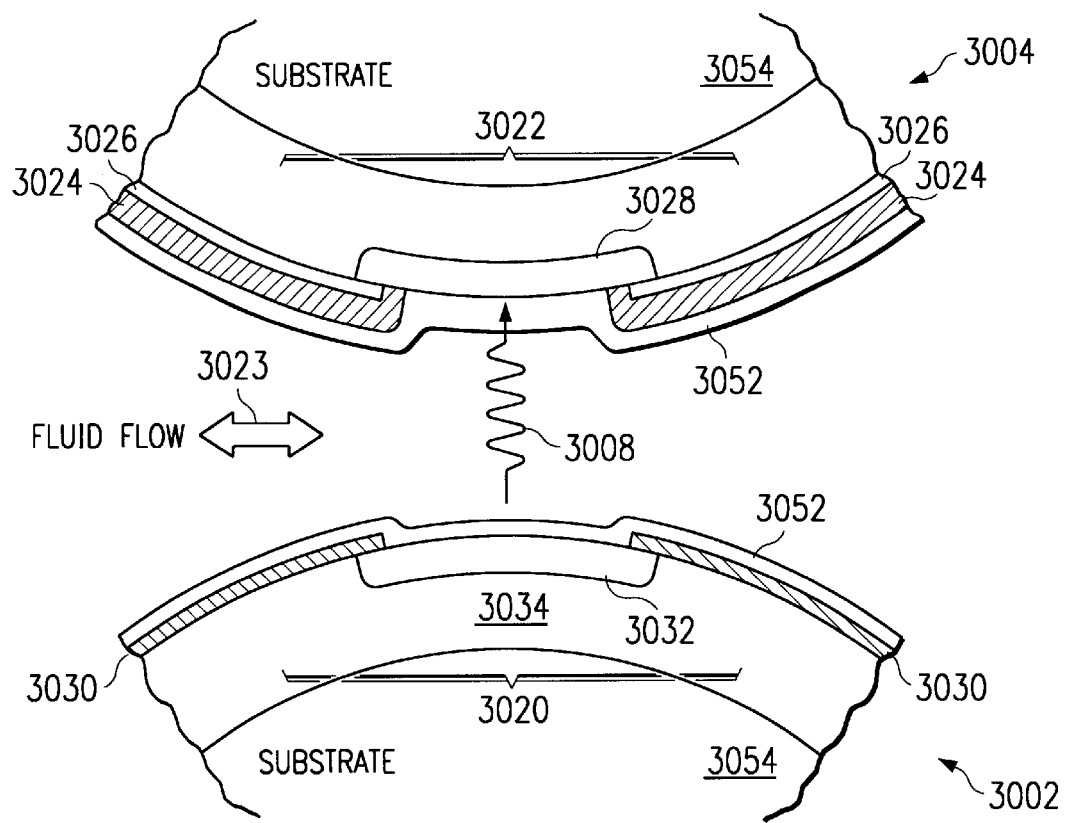
FIG. 30B illustrates a semiconductor structure for an LED sensing system for measuring fluid flow in a luminal structure.

Referring now to FIG. 30B, there is illustrated the semiconductor structure for an LED sensing system for measuring fluid flow. The light emitting diode ball 3002 emits light 3008 (or other energy) across the luminal region of the needle 3000 to a light detecting ball 3004. It is desirable that the balls 3002 and 3004 should be installed substantially perpendicular to the radial axis of the needle, and aligned with one another in opposite ends of a diametrical line of the needle 3000 such that the direction of light 3008 emitted from the emitter ball 3002 impinges a photodiode 3022 (or other receptor) of the detector ball 3004 in a direction which is substantially perpendicular to the flow 3023 of the fluid being measured. The light emitting diode structure 3020 of the emitter ball 3002 emits light which is dispersed across an area sufficient for the photodiode structure 3022 of the light detecting ball 3004 to detect. Each ball 3002 and 3004 is sealed with a thin exterior glass passivation layer 3052 (e.g., PSG) to provide isolation of the ball electronics from the body tissues and fluids being measured.

The detector structure 3022 of detector ball 3004 is commonly known, and can be conformed to the arcuate surface of the detector ball 3004 using conventional deposition and fabrication technique practices. For example, underlying the passivation layer 3052 are metal contacts 3024 for electrical interfacing. Underlying the metal contacts 3024 is an oxidation layer 3026 (e.g., $SiO_2$). The metal contacts 3024 contact a diffused region 3028, which may be a p+region, in this particular embodiment. Underlying the $p^+$-doped region 3028 lies a n-doped region 3029, followed by the substrate 3054, which may a more heavily doped $n^+$ region.

The LED structure 3020 of emitter ball 3002 is also commonly known, and a wide variety of structures may be employed to obtain the desired results. For example, underlying the glass passivation layer 3052 are metal contacts 3030 which contact a diffused region 3032. The diffused region 3032 may be a p⁺ region diffused in an n-type region 3034 which overlies the more heavily n⁺-doped substrate 3054. Note that the photo structures are not limited to diodes, but may also be phototransistor structures.

Figure 30C:
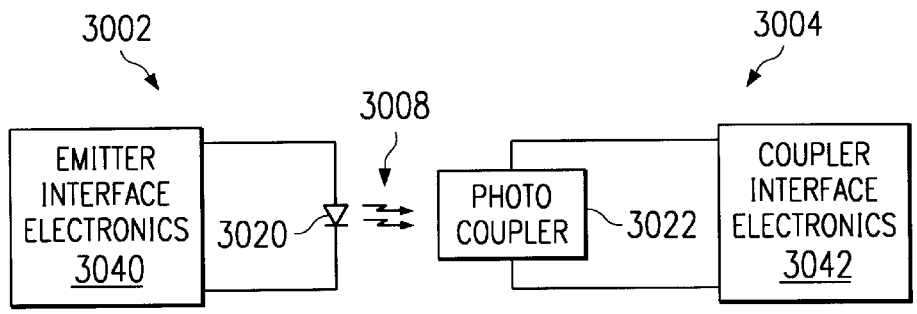
FIG. 30C illustrates a conventional LED circuit having an emitter and coupler.

Referring now to FIG. 30C, there is illustrated a conventional circuit diagram of the LED/photodiode circuit as fabricated and illustrated in FIG. 30B. As mentioned hereinabove, the emitter ball 3002 comprises the LED emitter electronics 3040, which LED 3020 interfaces to emitter interface electronics 3040. In operation, the emitter interface electronics 3040 drives the LED 3020 to emit light 3008 which impinges on a photocoupler 3022 fabricated into the photo detector ball 3004. The photocoupler 3022 outputs a voltage in proportion to the light intensity of the source LED 3020, which voltage signals are fed into coupler interface electronics 3042 of the detector ball 3004. As mentioned hereinabove, the light 3008 is emitted from LED 3020 across the lumen having fluid flowing therethrough.

Figure 31:
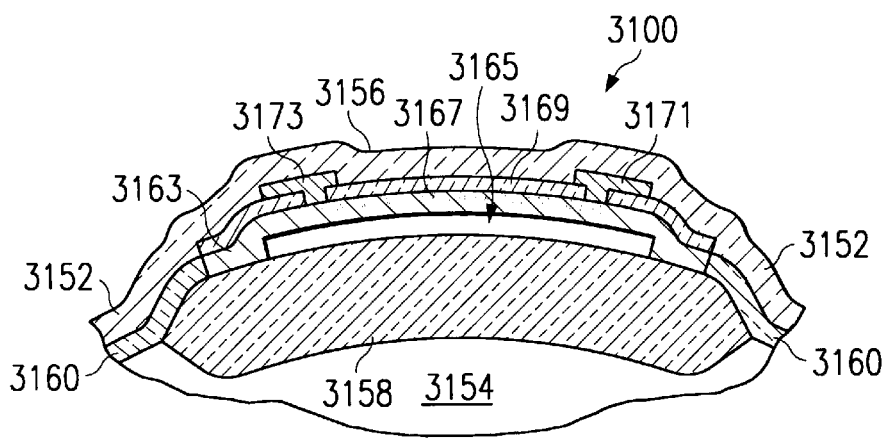
FIG. 31 illustrates a semiconductor structure of a strain gauge pressure sensor which may be used to measure pressure, according to a disclosed embodiment.

Referring now to FIG. 31, there is illustrated a semiconductor structure of a strain gauge pressure sensor which may be used to measure pressure at the tip of the needle. By way of example, the sensor 3100 may consist of a strain gauge fabricated atop the field oxide layer 3158. A dome 3163 is supported at its periphery by the field oxide 3158 and defines a cavity 3165 between the dome and the field oxide 3158. The dome 3163 preferably comprises monocrystalline silicon and includes an elongated doped resistor 3167, which is indicated by the stippling at the outer surface of the silicon dome 3163. A dielectric layer 3169, such as silicon dioxide, overlies the dome 3163. Metal contacts 3171 and 3173 are formed atop the dielectric layer 3169 and extend therethrough to make contact with the opposite ends of the doped resistor 3167. The metal contacts 3171 and 3173 have extensions (not shown in the cross section) that interconnect the resistor with other circuitry providing excitation power to the sensor.

The strain gauge transducer 3100 can be fabricated by forming a layer of selectively etchable material in the shape of the cavity 3165 over the field oxide layer 3158. For example, a phosphorus doped oxide can be deposited on the surface of the device, and then patterned into the desired shape by photolithographic techniques adapted to the spherical shape of the device. Next, the silicon dome 3163 is formed, such as by the deposition of polycrystalline silicon followed by recrystallization. Alternatively, the monocrystalline silicon layer used to make the dome 3163 can be epitaxially grown, such as by seeding the growth from an exposed portion of the substrate 3154 adjacent to the field oxide 3158. Such techniques are known, as described in U.S. Pat. No. 4,754,314, entitled "Split-Level CMOS," issued Jun. 28, 1988. A patterning procedure is then used to define the ultimate shape of the periphery of the dome 3163. Then, peripheral ports (not shown) are etched at opposite sides of the dome 3163 down to the doped oxide layer. Next, the device is exposed to an acid that preferentially etches doped oxide at a much faster rate than undoped silicon dioxide. It is well known that hydrofluoric acid will etch phosphorus doped oxide at a much faster rate (e.g., 15 times faster) depending on the phosphorus doping level and oxide density. The acid flows into the peripheral ports and etches the doped oxide layer laterally beneath the silicon dome 3163 to create the cavity 3165. The acid is then flushed out to introduce air or other gas, such as nitrogen, into the cavity 3165. Then, the outer dielectric layer 3169 is formed followed by the contacts 3171 and 3173. The deposition of the silicon dioxide of the dielectric layer 3169 fills the peripheral ports and seals the cavity 3165.

In a variation of the foregoing technique, a thin silicon nitride layer (not shown) can be deposited on the field oxide layer 3158 to serve as an etch-stop layer, followed by the deposition and patterning of the selectively etchable oxide layer. Optionally, another thin silicon nitride layer can be deposited atop the patterned oxide layer prior to the formation of the silicon layer 3163. These additional steps can facilitate preferential lateral etching of the patterned oxide layer to create a cavity like the cavity 3165, since hydrofluoric acid etches oxide at a much faster rate (e.g., 50 times faster) than silicon nitride.

In operation, the strain gauge 3100 senses pressure applied to the dome 3163 through the dielectric layers 3152 and 3169. As the pressure increases, the dome 3163 flexes downward very slightly, which also compresses the gas in the cavity 3165 to a slight degree. The resistance of the resistor 3167 varies in proportion to the variations in pressure of the fluid adjacent the outer surface 3156 of the dielectric layer 3152. The characteristics of semiconductor strain gauges are known in the art. A semiconductor strain gauge whose essential characteristics are similar to the strain gauge 3100 of FIG. 31 is described in U.S. Pat. No. 4,618,844, entitled "Semiconductor Pressure Transducer," issued Oct. 21, 1986, which is hereby incorporated by reference Other techniques may be used to integrate a pressure transducer onto the surface of a semiconductor ball. For example, variable capacitors, which are ideally suited for sensing pressure, can be fabricated using conventional semiconductor fabrication processes. A method of making a variable capacitor semiconductor transducer is described in U.S. Pat. No. 4,665,610, entitled "Method of Making a Semiconductor Transducer Having Multiple Level Diaphragm Structure," issued May 19, 1987, which is hereby incorporated by reference. Such a method or variations thereof can be adapted for fabrication on a spherical-shaped semiconductor substrate.

Figure 32:
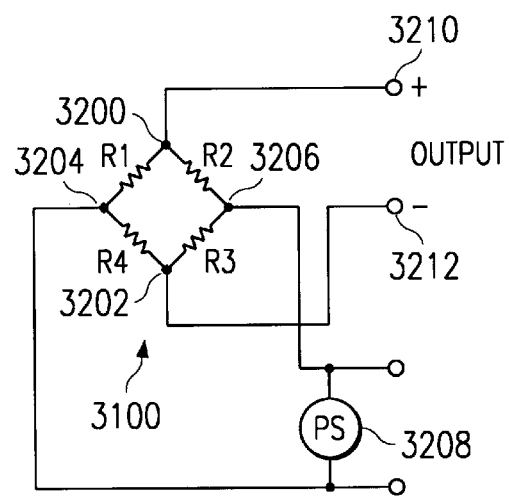
FIG. 32 illustrates a conventional strain gauge circuit according to the device structure of FIG. 31.

Referring now to FIG. 32, there is illustrated a conventional strain gauge circuit according to the device structure of FIG. 31. A conventional strain gauge architecture comprises a set of four resistances in the configuration of a Wheatstone bridge. Resistances R1, R2, R3 and R4 are connected end-to-end in a loop such that the output signals are extracted from opposing nodes 3200 (a node common to resistances R1 and R2) and node 3202 (a node common to resistances R3 and R4). In like fashion, the excitation voltage is applied at the remaining two opposing nodes 3204 (the point common between resistances R1 and R4) and node 3206 (the point common to resistances R2 and R3). The excitation voltage is supplied by a power source 3208 placed across the nodes 3204 and 3206. In the context of FIG. 31, the consolidation of resistances R1, R2, R3 and R4 represent the elongated doped resistor 3167 illustrated in FIG. 31. The elongated doped resistor 3167 may be tapped off at various points to obtain the illustrated Wheatstone bridge. The metal contacts 3171 and 3173 of FIG. 31 relate to the output terminals 3210 and 3212 which interface with a processor. The power source 3208 may comprise a miniature self-contained battery system, as described hereinabove, or may be provided remotely from the control system 140 coupled into the ball 110 through antenna 128 and provided through power regulator 130 to the strain gauge transducer 126 (similar to transducer 3100). When under strain, the elongated doped resistor 3167 flexes such that resistance values R1, R2, R3 and R4 are changed in proportion to the changing condition sensed. The output at nodes 3210 and 3212 is a voltage which varies in direct relationship to the parameter being measured by the strain gauge transducer 3100.

In a further embodiment, it can be appreciated that the disclosed drug delivery system may comprise a multi-compartment reservoir, or multiple reservoirs, e.g., a two-part reservoir (or two reservoirs) containing binary drugs, i.e. two drugs or fluids that interact with each other upon delivery to form a third composition which performs a certain function. Similarly, it can be appreciated that the disclosed reservoir concept could be replaced with a small vessel to contain a gas for delivery, and furthermore, a two-part vessel for the mixing and delivery of binary gases, where such applications are desirable.

Although the preferred embodiment has been described in detail, it should be understood that various changes, substitutions and alterations can be made therein without departing from the spirit and scope of the invention as defined by the appended claims.

What is claimed is:

1. A system for delivering a drug to a patient, comprising:
   a drug storage medium for storing a drug; and
   one or more aggregations of semiconductor devices operatively connected to said drug storage medium for monitor and control of the dispensing of the drug;
   wherein the system is implanted in the body of the patient at a drug delivery site for delivery of the drug to said site wherein said semiconductor devices are substantially spherical in shape.

2. The system of claim 1, wherein a first aggregate of said semiconductor devices performs a sensing function and a second aggregate of said semiconductor devices performs a control function to control dispensing of the drug.

3. The system of claim 2, wherein said second aggregation communicates with a remote control station to obtain power, and operatively connects with said first aggregation to receive sensor data for facilitating delivery of the drug.

4. The system of claim 3, wherein said remote control station is external to the body of the patient, and comprises a display for presenting information to an operator.

5. The system of claim 3, wherein said remote control station is implanted in the body of the patient proximate to the drug delivery system.

6. The system of claim 5, wherein said remote control station is implanted in the body remotely from the drug delivery system such that said remote control station communicates with the drug delivery system to control delivery of the drug to the said site.

7. The system of claim 1, wherein said one or more aggregations operate independently of a remote control station where power is supplied by an onboard battery source and operation of the system is controlled by a program stored local to said one or more aggregations and executed locally by a processor.

8. The system of claim 1, wherein said one or more aggregations provide a stimulus function in cooperation with delivery of the drug.

9. The system of claim 1, wherein said storage medium is a polyelectrolytic hydrogel covalently attached to the surface of one or more of said one or more aggregations of semiconductor devices, and which operates to inhibit release of the drug when the surface polarity of said semiconductor device is positive, and promotes release of the drug when the surface polarity is negative.

10. A drug delivery device, comprising:
    a semiconductor device which is miniature in size and substantially spherical in shape; and
    a drug storage medium attached to said semiconductor device;
    wherein the drug delivery device is implanted in a patient for controlled release of the drug.

11. The device of claim 10, wherein said drug storage medium is a polyelectrolytic hydrogel which is covalently attached to the surface of said semiconductor device, and surrounds said semiconductor device.

12. The device of claim 11, wherein said hydrogel has a negative polarity, and promotes the release of the drug when the surface polarity of said semiconductor device is negative, and inhibits the release of the drug when the surface polarity of said semiconductor device is positive.

13. A drug delivery system for delivering a drug to a patient, comprising:
    a miniature semiconductor device with circuitry for receiving power and control signals by RF transmission from a remote station;
    a drug storage medium incorporated with said semiconductor device and operating under the control of said semiconductor device;
    wherein said semiconductor device is implanted with said drug storage medium in a patient's body; and
    wherein signals from said remote station are transmitted to said semiconductor device to controllably direct delivery of the drug from said drug storage medium into said patient's body wherein said semiconductor device is sperically shaped.

14. The system of claim 13, wherein a condition is sensed within said patient's body and communicating data representative of said sensed condition by RF signals from semiconductor device to said remote station for monitoring and controlling the drug delivery in accordance therewith.

15. The system of claim 14, wherein said drug delivery medium comprises a hydrogel coating on the surface of said semiconductor device.

16. The system of claim 14, wherein said drug delivery medium comprises a subcutaneous reservoir controlled by said semiconductor device.

* * * * *